(12) United States Patent
Weiss et al.

(10) Patent No.: US 11,826,011 B2
(45) Date of Patent: Nov. 28, 2023

(54) CORTICAL RECORDING AND SIGNAL PROCESSING METHODS AND DEVICES

(71) Applicant: Thomas Jefferson University, Philadelphia, PA (US)

(72) Inventors: Shennan Aibel Weiss, Philadelphia, PA (US); Zachary Waldman, Philadelphia, PA (US); Michael Sperling, Philadelphia, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 642 days.

(21) Appl. No.: 16/622,098

(22) PCT Filed: Jun. 13, 2018

(86) PCT No.: PCT/US2018/037342
§ 371 (c)(1),
(2) Date: Dec. 12, 2019

(87) PCT Pub. No.: WO2018/231989
PCT Pub. Date: Dec. 20, 2018

(65) Prior Publication Data
US 2021/0145347 A1    May 20, 2021

Related U.S. Application Data

(60) Provisional application No. 62/519,561, filed on Jun. 14, 2017.

(51) Int. Cl.
*A61B 5/374* (2021.01)
*A61B 5/384* (2021.01)
(Continued)

(52) U.S. Cl.
CPC .............. *A61B 5/374* (2021.01); *A61B 5/384* (2021.01); *A61N 1/36025* (2013.01); *A61N 1/36171* (2013.01)

(58) Field of Classification Search
CPC ......... A61B 5/374; A61B 5/384; A61B 5/291; A61B 5/369; A61B 5/377; A61B 5/726;
(Continued)

(56) References Cited

U.S. PATENT DOCUMENTS 6,309,361 B1    10/2001    Thornton
2007/0043401 A1    2/2007    John
(Continued)

FOREIGN PATENT DOCUMENTS

WO    2016110804 A1    7/2016
WO    2018017655 A1    1/2018

OTHER PUBLICATIONS

Benjamini, Y., et al., "Controlling the False Discovery Rate: A Practical and Powerful Approach to Multiple Testing", Journal of the Royal Statistical Society, Series B (Methodological), vol. 57, No. 1, pp. 289-300, 1995.
(Continued)

*Primary Examiner* — Tse W Chen
*Assistant Examiner* — Clarissa Cuevas
(74) *Attorney, Agent, or Firm* — Cozen O'Connor

(57) ABSTRACT

A device and a signal processing method that can monitor human memory performance by recognizing and characterizing high-gamma (65-250 Hz) and beta (14-30 Hz) band oscillations in the left Brodmann Area 40 (BA40) of the brain that correspond with the strength of memory encoding or correct recall. The signal processing method detects high-gamma and beta band oscillations in the electrical signals recorded from left BA40, and quantifies the spectral content, power, duration, onset, and offset of the oscillations. The oscillation's properties are used to classify the subject's memory performance on the basis of a comparison with the subject's prior human memory performance and the properties of the corresponding oscillations. A report of the (Continued)

subject's current memory performance can be utilized in a closed loop brain stimulation device that serves the purpose of enhancing human memory performance.

11 Claims, 18 Drawing Sheets

(51) Int. Cl.
*A61N 1/36* (2006.01)
*A61B 5/291* (2021.01)
*A61B 5/369* (2021.01)
*A61B 5/377* (2021.01)
*A61B 5/00* (2006.01)

(58) Field of Classification Search
CPC ............ A61N 1/36025; A61N 1/36171; A61N 1/36082; A61N 1/36139
See application file for complete search history.

(56) References Cited

U.S. PATENT DOCUMENTS

| | | | |
|---|---|---|---|
| 2009/0024050 A1* | 1/2009 | Jung | A61B 5/4064 600/544 |
| 2013/0295016 A1 | 11/2013 | Gerber et al. | |
| 2014/0107728 A1 | 4/2014 | Itzhak et al. | |
| 2016/0220836 A1 | 8/2016 | Parks | |
| 2018/0021579 A1 | 1/2018 | Kahana et al. | |

OTHER PUBLICATIONS

Canolty, R.T., et al., "High Gamma Power is Phase-Locked to Theta Oscillations in Human Neocortex", Science, vol. 313, No. 5793, pp. 1626-1628, 2006.

Ezzyat, Y., et al., "Closed-loop stimulation of temporal cortex rescues functional networks and improves memory", Nature Communications, vol. 9, No. 365, 8 pages, 2018.

Gonzalez, J-F, et al., "ALMA images of discs: are all gaps carved by planets?", MNRAS, vol. 54, pp. L36-L40, 2015.

Lee, C-F, et al., "Formation and Atmosphere of Complex Organic Molecules of the HH 212 Protostellar Disk", The Astrophysical Journal, vol. 843, No. 27, 14 pages, 2017.

Lundqvist, M., et al., "Gamma and Beta Bursts Underlie Working Memory", Neuron, vol. 90, No. 1, pp. 152-164, 2016.

Maris, E., et al., "Nonparametric statistical testing of EEG- and MEG-data", Journal of Neuroscience Methods, vol. 164, No. 1, pp. 177-190, 2007.

Oostenveld, R., et al., "FieldTrip: Open Source Software for Advanced Analysis of MEG, EEG, and Invasive Electrophysiological Data", Computational Intelligence and Neuroscience, Article ID 156869, 9 pages, 2011.

Rutishauser, U., et al., "Single-Neuron Representation of Memory Strength and Recognition Confidence in Left Human Posterior Parietal Cortex", Neuron, vol. 97, No. 1, pp. 209-220, 2018.

Berto, et al. "Human Genomic Signatures of Brain Oscillations During Memory Encoding," Cerebral Cortex, Publication Online, May 2018, retrieved from the internet https://trans-cranial.com/local/manuals/cortical_functions_rev_v1_0_.pdf.

International Search Report and Written Opinion in International Application No. PCT/US2018/037342 dated Sep. 27, 2018, International Searching Authority United States.

* cited by examiner

FIG. 1

| Location | RippleOn-Spike | Spike | Ripple | Location | RippleOn-Spike | Spike | Ripple |
|---|---|---|---|---|---|---|---|
| L-Amygdala | P=0.34, p=0.8635, n=96 | P=1.78, p=0.7940, n=1133 | P=8.54, p=0.3015, n=4 | L-Brodmann area 28 | P=-9.42, p=0.2070, n=67 | P=-3.80, p=0.6910, n=922 | P=-10.17, p=0.0390, n=4 |
| L-Brodmann area 1_2_3_5 | P=-12.45, p=0.0145, n=6 | P=-3.81, p=0.2740, n=28 | P=1.09, p=0.9990, n=1 | L-Brodmann area 30 | P=8.32, p=0.5535, n=14 | P=5.78, p=0.9515, n=104 | P=20.69, p=0.1050, n=4 |
| L-Brodmann area 4_6 | P=17.24, p=0.2490, n=15 | P=8.58, p=0.9835, n=248 | P=-0.05, p=0.0025, n=0 | L-Brodmann area 31 | P=-4.25, p=0.2750, n=53 | P=-4.64, p=0.3170, n=179 | P=-1.25, p=0.4575, n=13 |
| L-Brodmann area 7 | P=7.37, p=0.1940, n=94 | P=-1.59, p=0.1135, n=129 | P=18.30, p=0.1675, n=6 | L-Brodmann area 34 | P=3.86, p=0.4395, n=5 | P=-5.03, p=0.3485, n=240 | P=-8.92, p=0.0880, n=4 |
| L-Brodmann area 9 | P=16.47, p=0.1420, n=5 | P=-3.05, p=0.1780, n=53 | P=-7.72, p=0.6805, n=9 | L-Brodmann area 35 | P=-13.24, p=0.0160, n=22 | P=-4.30, p=0.0095, n=167 | P=17.95, p=0.0690, n=2 |
| L-Brodmann area 10 | P=0.27, p=0.2060, n=20 | P=9.32, p=0.0480, n=67 | P=-2.03, p=0.5415, n=6 | L-Brodmann area 36 | P=-11.87, p=0.0055, n=77 | P=-2.09, p=0.2840, n=200 | P=-13.14, p=0.0295, n=41 |
| L-Brodmann area 11 | P=-2.01, p=0.8250, n=20 | P=-13.65, p=0.00635, n=72 | P=-17.11, p=0.0080, n=20 | L-Brodmann area 37 | P=3.17, p=0.8355, n=116 | P=-7.64, p=0.6830, n=603 | P=-17.59, p=0.0820, n=19 |
| L-Brodmann area 13 | P=6.14, p=0.6075, n=65 | P=8.53, p=0.9600, n=414 | P=17.38, p=0.3275, n=24 | L-Brodmann area 38 | P=-13.31, p=0.1805, n=114 | P=-13.59, p=0.0135, n=503 | P=-2.42, p=0.5565, n=11 |
| L-Brodmann area 18 | P=5.37, p=0.4425, n=1 | P=14.07, p=0.7580, n=32 | P=15.75, p=0.2940, n=5 | L-Brodmann area 39 | P=2.82, p=0.9295, n=221 | P=20.41, p=0.3325, n=357 | P=-4.74, p=0.2610, n=12 |
| L-Brodmann area 19 | P=15.11, p=0.9650, n=155 | P=17.71, p=0.7185, n=531 | P=3.40, p=0.3185, n=12 | L-Brodmann area 40 | P=12.88, p=0.4710, n=111 | P=0.29, p=0.7240, n=296 | P=18.10, p=0.0380, n=53 |
| L-Brodmann area 20 | P=-2.68, p=0.9680, n=124 | P=-10.28, p=0.0600, n=660 | P=-5.14, p=0.7255, n=68 | L-Brodmann area 41_42 | P=-7.25, p=0.0925, n=9 | P=4.43, p=0.6260, n=53 | P=9.22, p=0.7640, n=3 |
| L-Brodmann area 21 | P=-2.88, p=0.0975, n=311 | P=-3.29, p=0.0000, n=1379 | P=-14.68, p=0.0505, n=153 | L-Brodmann area 43 | P=-4.05, p=0.6555, n=2 | P=-6.20, p=0.0060, n=114 | P=-0.05, p=0.0025, n=0 |
| L-Brodmann area 22 | P=0.83, p=0.7435, n=91 | P=2.12, p=0.9885, n=457 | P=-2.99, p=0.1895, n=16 | L-Brodmann area 45 | P=-12.36, p=0.6250, n=16 | P=-17.85, p=0.3545, n=26 | P=-12.36, p=0.6385, n=16 |
| L-Brodmann area 27 | P=16.42, p=0.1015, n=3 | P=-2.05, p=0.6530, n=36 | P=-0.63, p=0.6250, n=2 | L-Brodmann area 47 | P=-23.89, p=0.0005, n=26 | P=-12.04, p=0.3865, n=143 | P=-7.13, p=0.4555, n=13 |

FIG. 2

| Location | RippleOn-Spike | Spike | Ripple | Location | RippleOn-Spike | Spike | Ripple |
|---|---|---|---|---|---|---|---|
| L-Caudate Tail | P=-1.02, p=0.6980, n=51 | P=-14.31, p=0.0005, n=147 | P=0.62, p=0.9025, n=21 | R-Brodmann area 13 | P=-16.67, p=0.0185, n=22 | P=-3.70, p=0.2690, n=218 | P=-3.84, p=0.3365, n=13 |
| L-Corpus Callosum | P=12.81, p=0.3165, n=3 | P=1.13, p=0.9490, n=72 | P=6.12, p=0.5935, n=1 | R-Brodmann area 20 | P=-0.24, p=0.2235, n=157 | P=-1.35, p=0.0310, n=883 | P=8.87, p=0.1085, n=55 |
| L-Hippocampus | P=-6.88, p=0.1345, n=193 | P=-5.82, p=0.3805, n=898 | P=-1.76, p=0.3280, n=30 | R-Brodmann area 21 | P=0.53, p=0.4220, n=86 | P=-3.12, p=0.1195, n=1082 | P=2.55, p=0.1125, n=44 |
| L-Optic Tract | P=-10.22, p=0.1430, n=8 | P=-4.71, p=0.3220, n=90 | P=-0.05, p=0.0025, n=0 | R-Brodmann area 22 | P=6.09, p=0.6640, n=7 | P=2.15, p=0.8560, n=185 | P=-0.05, p=0.0025, n=0 |
| L-Pulvinar | P=16.09, p=0.4455, n=22 | P=20.70, p=0.1695, n=20 | P=-0.05, p=0.0025, n=0 | R-Brodmann area 23 | P=15.73, p=0.3760, n=2 | P=-9.41, p=0.1045, n=74 | P=2.84, p=0.6055, n=2 |
| L-Putamen | P=-4.80, p=0.2310, n=7 | P=-4.47, p=0.1655, n=100 | P=6.46, p=0.4340, n=1 | R-Brodmann area 24 | P=18.42, p=0.0730, n=6 | P=-1.11, p=0.6330, n=264 | P=18.42, p=0.0635, n=4 |
| R-Amygdala | P=2.90, p=0.6310, n=105 | P=4.73, p=0.5000, n=450 | P=2.69, p=0.1085, n=71 | R-Brodmann area 27 | P=3.37, p=0.5070, n=1 | P=-9.92, p=0.3845, n=55 | P=-0.05, p=0.0025, n=0 |
| R-Brodmann area 1_2_3_5 | P=-0.98, p=0.6430, n=6 | P=-7.13, p=0.5290, n=66 | P=20.38, p=0.3610, n=2 | R-Brodmann area 28 | P=-8.41, p=0.3120, n=22 | P=-6.88, p=0.5060, n=136 | P=3.47, p=0.5020, n=1 |
| R-Brodmann area 4_6 | P=0.31, p=0.7025, n=9 | P=-2.68, p=0.1405, n=109 | P=6.44, p=0.4335, n=1 | R-Brodmann area 31 | P=-4.06, p=0.4260, n=25 | P=-14.21, p=0.0270, n=286 | P=8.75, p=0.3265, n=1 |
| R-Brodmann area 7 | P=-17.81, p=0.0970, n=25 | P=-16.13, p=0.1670, n=147 | P=-6.30, p=0.2305, n=4 | R-Brodmann area 32 | P=-0.05, p=0.0025, n=0 | P=-12.67, p=0.0095, n=33 | P=-5.99, p=0.4045, n=1 |
| R-Brodmann area 8 | P=-13.29, p=0.0165, n=5 | P=13.04, p=0.0230, n=62 | P=15.27, p=0.1905, n=5 | R-Brodmann area 35 | P=21.06, p=0.2670, n=4 | P=-8.82, p=0.0600, n=65 | P=2.16, p=0.6355, n=5 |
| R-Brodmann area 9 | P=0.86, p=0.3595, n=18 | P=-10.49, p=0.5770, n=97 | P=5.35, p=0.2055, n=24 | R-Brodmann area 36 | P=-18.80, p=0.0225, n=74 | P=-9.09, p=0.5930, n=231 | P=-6.27, p=0.3505, n=7 |
| R-Brodmann area 10 | P=13.11, p=0.0680, n=10 | P=-5.39, p=0.8965, n=81 | P=-3.32, p=0.3245, n=2 | R-Brodmann area 37 | P=-7.53, p=0.1780, n=7 | P=-2.27, p=0.2440, n=96 | P=-4.94, p=0.4060, n=6 |
| R-Brodmann area 11 | P=-3.96, p=0.4870, n=7 | P=8.19, p=0.4400, n=20 | P=20.51, p=0.4440, n=2 | R-Brodmann area 38 | P=-13.80, p=0.0225, n=38 | P=-7.93, p=0.0040, n=266 | P=-7.77, p=0.5335, n=26 |

FIG. 3

| Location | RippleOn-Spike | Spike | Ripple |
|---|---|---|---|
| R-Brodmann area 40 | P=0.06, p=0.3515, n=29 | P=3.27, p=0.2590, n=264 | P=13.61, p=0.2590, n=5 |
| R-Brodmann area 47 | P=-3.17, p=0.5925, n=47 | P=14.35, p=0.2950, n=259 | P=4.71, p=0.1360, n=21 |
| R-Caudate Tail | P=-11.15, p=0.0090, n=44 | P=-4.12, p=0.0540, n=176 | P=8.32, p=0.0995, n=6 |
| R-Corpus Callosum | P=-12.76, p=0.1575, n=11 | P=16.62, p=0.0075, n=156 | P=4.76, p=0.4445, n=1 |
| R-Hippocampus | P=2.07, p=0.2765, n=40 | P=-3.63, p=0.1660, n=257 | P=7.83, p=0.6040, n=17 |
| R-Putamen | P=12.57, p=0.2295, n=9 | P=6.85, p=0.4780, n=74 | P=1.12, p=0.5560, n=1 |

FIG. 4

| Subject | No. of Depths | No. of Grids | No. of Strips | Total No. of Electrodes | Age | Gender | Patient demographic information - Site of epilepsy | Tasks | Recall percentage | No. of trials |
|---|---|---|---|---|---|---|---|---|---|---|
| R1003P | | | | 1 | 38F | | L anterior temporal lobe | FR1 | 0.33 | 564 |
| R1021D | | 1 | | 1 | 24M | | R mesial temporal lobe and L temporal and parietal regions (from electrode notes) | CatFR1 | 0.29 | 300 |
| R1022J | 2 | | | 2 | | | Cingulate region | FR1 | 0.27 | 300 |
| R1026D | | 10 | | 10 | 24 | | L anterior temporal lobe; rare L occipital/subocciptal regions | CatFR1/FR1 | .33/.23 | 192/300 |
| R1036M | 6 | 2 | 4 | 6 | 49M | | L anterior and mesial temporal regions | CatFR1/FR1 | .16 | 276/300 |
| R1049J | | | | 6 | 58F | | L anterior to mid hippocampal region | CatFR1/FR1 | .08 | 300 |
| R1052E | | | 1 | 1 | 19F | | Non-diagnostic phase II study | CatFR1/FR1 | .28 | 400 |
| R1053J/1 | 4 | 14 | 4 | 4 | 44F | | L and R temporal lobes | CatFR1/FR1 | .08 | 444/408 |
| R1059J | | | | | 34F | | L and R temporal lobes | CatFR1/FR1 | .65/.34 | 200/800 |
| R1065J | | 22 | | 22 | 44F | | L anterior and inferior temporal regions | CatFR1/FR1 | .2/.17 | 600/768 |
| R1067P | | | | | 44F | | L anterior lateral frontal region and L parietal region | CatFR1/FR1 | .49/.29 | 300/300 |
| R1069M | | | | 5 | 26M | | L mesial temporo-occipital region | CatFR1/FR1 | .16 | 696 |
| R1070T | 5 | | | 8 | 40F | | Non-diagnostic phase II study | CatFR1/FR1 | .27/.19 | 300/384 |
| R1074M | 8 | | | 22 | 24M | | Non-diagnostic phase II study | FR1 | .28 | 300 |
| R1080E | | | | 5 | 42F | | L medial primary sensory cortex | CatFR1/FR1 | .3/.2 | 216/180 |
| R1084T | 3 | 27 | | 30 | 25M | | L anterior lobe | CatFR1/FR1 | .03 | 300/900 |
| R1086M | | 4 | 4 | 4 | 20M | | Non-diagnostic phase II study | FR1 | .22 | 372 |
| R1089P | | | | | 47M | | Unclear (missing pages) | CatFR1 | .03 | 300 |
| R1094T | 26 | | | 26 | 43F | | L mesial temporal lobe | CatFR1/FR1 | .32/.25 | 360/300 |
| R1100D | | 1 | | 4 | 25F | | Bilateral mesial temporal areas | CatFR1 | .57 | 540 |
| R1101T | | | | 2 | 34M | | Occipital region (from electrode notes) | CatFR1/FR1 | .58/.54 | 444/1020 |
| R1102P | 2 | 12 | 4 | 12 | 20M | | L anterior temporal and parieto-occipital regions | CatFR1/FR1 | .42/.24 | 300/300 |
| R1111M | | | 3 | 14 | 31F | | posterior temporal and parietal regions | FR1 | .03 | 600 |
| R1120E | 14 | | | | 33F | | posterior subtemporal region | CatFR1 | .85 | 600 |
| R1124J | | | | 2 | 44F | | R mesial temporal lobe | FR1 | .02 | 516 |
| R1125T | 3 | 12 | 3 | 24 | 57M | | Non-diagnostic phase II study | CatFR1/FR1 | .28/.2 | 120/408 |
| R1127P | | 16 | 6 | 7 | 64M | | L mesial and lateral superior frontal regions | CatFR1/FR1 | .24/.09 | 840 |
| R1134T | 6 | | 1 | 2 | 47M | | L inferior parieto-occipital region | CatFR1/FR1 | .14/.09 | 1344/1200 |
| R1135E | 8 | | | 3 | 40M | | Non-diagnostic phase II study | CatFR1/FR1 | .19/.17 | 720/300 |
| R1147P | 4 | | | 4 | 38M | | anterior hippocampus; R mesial temporal lobe | FR1 | .12 | 900 |
| R1163T | | 15 | | 15 | 23F | | posterior temporal region | FR1 | .24 | 396 |
| R1177M | | | | | | | L mesial temporal, temporal and limbic regions (from electrode notes) | | | |
| R1221P | | 10 | | 10 | M | | L temporal, frontal, temporo-occipital regions (from electrode notes) | CatFR1/FR1 | .28/.9 | 900/300 |
| R1291M | 18 | | | 18 | | | | CatFR1/FR1 | .54/.36 | 600/300 |
| TJ082 | | | | 1 | 57F | | | FR1 | 0.23 | 576 |

FIG. 11
Classification of Recall Performance Based on High Gamma and Beta Oscillations During Corresponding Encoding Epoch

| Subject | AUROC | Task | #Electrodes used | Electrode types |
|---|---|---|---|---|
| R1003P | 0.68 | FR1 | 1 | 1 subdural |
| R1059J | 0.68 | FR1 | 1 | 1 subdural |
| R1069M | 0.66 | CatFR1 | 3 | 3 subdural |
| R1069M | 0.67 | FR1 | 5 | 5 subdural |
| R1084T | 0.66 | FR1 | 10 | 1 depth/9 subdural |
| R1094T | 0.76 | FR1 | 12 | 12 depth |
| R1094T | 0.75 | CatFR1 | 12 | 12 depth |
| R1102P | 0.71 | CatFR1 | 2 | 2 subdural |
| R1138T | 0.61 | CatFR1 | 3 | 3 depth |
| R1036M | 0.62 | FR1 | 4 | 4 subdural |
| R1107J | 0.59 | CatFR1 | 2 | 2 depth |
| R1114C | 0.61 | FR1 | 6 | 6 depth |
| R1134T | 0.64 | FR1 | 3 | 3 depth |
| R1221P | 0.57 | CatFR1 | 5 | 5 subdural |
| R1221P | 0.60 | FR1 | 4 | 4 subdural |
| R1291M | 0.57 | CatFR1 | 5 | 5 subdural |

FIG. 14
Correlation between High Gamma Power and Recall Number

| Subject | Task | Electrode | Recall percentage | R-squared | P-value | Slope of fit |
|---|---|---|---|---|---|---|
| R1067P | RAM_FR1 | LG37-LG38 | 0.17 | 0.229278289 | 6.27E-05 | -2.36 |
| R1067P | RAM_FR1 | LG40-LG48 | 0.17 | 0.125540506 | 0.004072497 | -0.82 |
| R1114C | RAM_CatFR1 | PPC7-PPC8 | 0.42 | 0.313051741 | 0.003637196 | 0.01 |
| R1065J | RAM_CatFR1 | LS15-LS16 | 0.65 | 0.214590959 | 1.21E-06 | 0.12 |
| R1065J | RAM_CatFR1 | LS12-LS13 | 0.65 | 0.264069667 | 4.55E-08 | 0.21 |
| R1069M | RAM_CatFR1 | LFPG47-LFPG48 | 0.49 | 0.452444759 | 0.000229836 | 0.81 |
| R1074M | RAM_FR1 | LY11-LY12 | 0.19 | 0.347669908 | 0.001922549 | 0.07 |
| R1074M | RAM_CatFR1 | LY11-LY12 | 0.27 | 0.467568682 | 0.000164219 | 0.08 |
| R1074M | RAM_CatFR1 | LY10-LY11 | 0.27 | 0.458537715 | 0.000200933 | 0.20 |
| R1094T | RAM_CatFR1 | LU6-LU7 | 0.12 | 0.311013004 | 0.003773277 | 0.14 |
| R1094T | RAM_FR1 | LX9-LX10 | 0.12 | 0.133568323 | 0.001263177 | 0.23 |
| R1094T | RAM_FR1 | LX8-LX9 | 0.12 | 0.209647451 | 3.62E-05 | 0.28 |
| R1111M | RAM_CatFR1 | LPOG5-LPOG13 | 0.58 | 0.485628327 | 1.66E-06 | 0.22 |
| R1111M | RAM_CatFR1 | LPOG13-LPOG14 | 0.58 | 0.47112456 | 2.73E-06 | 0.27 |
| R1111M | RAM_CatFR1 | LPOG32-LPOG40 | 0.58 | 0.354172147 | 0.000102304 | 0.56 |
| R1111M | RAM_CatFR1 | LPOG14-LPOG15 | 0.58 | 0.447031092 | 6.10E-06 | 0.87 |
| R1114C | RAM_CatFR1 | PPC8-PPC9 | 0.42 | 0.392192906 | 0.000811061 | 0.03 |
| R1114C | RAM_FR1 | PPC8-PPC9 | 0.24 | 0.355372388 | 0.001661977 | 0.04 |
| R1114C | RAM_CatFR1 | PPC10-PPC11 | 0.42 | 0.374703302 | 0.001145554 | 0.06 |
| R1114C | RAM_FR1 | PPC9-PPC10 | 0.24 | 0.393685077 | 0.000787202 | 0.09 |
| R1114C | RAM_FR1 | PPC10-PPC11 | 0.24 | 0.384057619 | 0.000953385 | 0.11 |
| R1114C | RAM_FR1 | PPC11-PPC12 | 0.24 | 0.452222459 | 0.00023096 | 0.23 |
| R1135E | RAM_CatFR1 | LROI2d1-LROI2d3 | 0.15 | 0.238969134 | 0.000315646 | 0.58 |
| R1177M | RAM_FR1 | LG63-LG64 | 0.24 | 0.300162592 | 0.000965581 | 1.09 |

Correlation between High Gamma Power and Recall Number

FIG. 16
Correlation between Beta Power and Recall Number

| Subject | Task | Electrode | Recall percentage | R-squared | P-value | Slope of fit |
|---|---|---|---|---|---|---|
| R1069M | RAM_FR1 | LFPG16-LFPG24 | 0.29 | 0.394890384 | 0.000768406 | -35.398701 |
| R1177M | RAM_FR1 | LG54-LG55 | 0.24 | 0.316835947 | 0.000649415 | -15.211467 |
| R1111M | RAM_FR1 | LPOG23-LPOG31 | 0.54 | 0.124170178 | 0.000941574 | -4.6723914 |
| R1111M | RAM_CatFR1 | LPOG5-LPOG13 | 0.58 | 0.335008603 | 0.000174848 | 3.04733004 |
| R1134T | RAM_FR1 | LP8-LP9 | 0.09 | 0.256443607 | 7.72E-06 | 5.93860248 |
| R1111M | RAM_CatFR1 | LPOG13-LPOG14 | 0.58 | 0.357796265 | 9.23E-05 | 10.4240026 |
| R1111M | RAM_CatFR1 | LPOG14-LPOG15 | 0.58 | 0.34728798 | 0.000124223 | 15.008074 |

CORTICAL RECORDING AND SIGNAL PROCESSING METHODS AND DEVICES

CROSS REFERENCE TO RELATED APPLICATIONS

This is an United States National Stage application of International Patent Application No. PCT/US2018/037342, filed Jun. 13, 2018, published as WO 2018/231989 on Dec. 20, 2018, which claims priority to U.S. Provisional Patent Application No. 62/519,561, filed Jun. 14, 2017, the entirety of each of which is incorporated herein by reference.

GOVERNMENT SUPPORT

This invention was made with Government support under Grant No. N66001-14-2-4032, awarded by Space and Naval Warfare Systems Center, Pacific; Grant No. NIH NS094633 awarded by the National Institutes of Health, and the DARPA Restoring Active Memory (RAM) program (Cooperative Agreement N66001-14-2-4032). The government has certain rights in the invention.

FIELD OF INVENTION

The present application is generally related to devices that monitor and stimulate human memory performance, specifically for stimulating the left inferior parietal lobe with a deep brain stimulating electrode. Said devices monitor human memory performance by analyzing and quantifying discrete electroencephalographic signals in the high gamma (65-250 Hz) and beta (14-30 Hz) band from the left Brodmann Area 40 of the brain that serve in themselves as biomarkers of human memory performance, and to transform the measurements of these biomarkers in to a report, or signals for biofeedback, brain-computer interface, or closed loop brain stimulation applications.

BACKGROUND OF THE INVENTION

In a biological context, memory involves the encoding, consolidation, and retrieval of sensory information. Poor memory performance affects at least 1 in 20 people over the age of 65. For those unaffected by memory disorders, memory performance is a key factor in determining occupational and educational fitness.

Determining an individual's memory performance currently requires neuropsychological testing. This testing provides a static measure of the individual's performance during the examination. To dynamically assess an individual's memory performance across time requires the identification and quantification of physiological signal(s) which are correlated with memory performance. Prior work has failed to identify a sufficiently accurate discrete and distinct physiological signal (i.e. biomarker) measured from a single brain area that can measure an individual's memory performance. Prior attempts to define signals with a subsequent memory effect do not utilize a brain generated biomarker, but rather derive or generate the biomarker of subsequent memory effect from continuous brain signals recorded from multiple brain areas that are not in themselves defined as biomarkers with a subsequent memory effect (US20180021579A1; Ezzyat et al., 2018). Meanwhile, others simply define rudimentary devices that can detect brain waves, but do not identify a biomarker (US 2013/0295016; Gerber et al; U.S. Pat. No. 6,309,361, Thronton).

SUMMARY OF THE INVENTION

A method for augmenting a patient diagnosed with impairment in working or episodic memory performance that efficaciously improves said performance consisting of: surgically implanting an electrode to said patient so that the distal end lies in electrical communication with the predetermined site in the left inferior parietal lobule; coupling the proximal end of the electrode to an electrical signal source; and operating said electrical signal source to stimulate a predetermined treatment site in the left inferior parietal lobule, whereby working and episodic memory performance is enhanced. In certain embodiments, the site includes the left angular gyms or the left supramarginal gyms. In certain embodiments, the site is left BA40.

In certain embodiments, the method above includes wherein operating said electrical signal source is controlled by a microprocessor. In certain further embodiments, wherein the microprocessor that operates the said electrical signal also processes electrical signals recorded from the said electrode.

In certain preferred embodiments, the method as described above, wherein the said patient has been diagnosed with mild cognitive impairment, dementia, traumatic brain injury, schizophrenia, or epilepsy.

In a preferred embodiment, a deep brain stimulating electrode, comprising an amplifier, a stimulator, microprocessor, memory storage system, Bluetooth® transceiver, and a battery; wherein said electrode is surgically placed into the inferior parietal lobule to provide electrical stimulation. In certain embodiments, the electrode has a diameter of about 0.86 mm, and electrode spacing every 5 mm.

A further embodiment is directed to a device or system and a signal processing method that can be used with a device or system that can recognize, distinguish, and characterize high-gamma (65-250 Hz) and beta oscillation (14-30 Hz) biomarkers in left Brodmann area 40 (BA40). These oscillations and their properties are used to classify the subject's memory performance. The classification of memory performance is determined on the basis of a comparison of the oscillations' properties with the subject's prior human memory performance and the properties of the oscillations corresponding to the past performance. The signal processing method can operate near real time, and can be utilized for closed loop brain stimulation, brain computer interface, or biofeedback.

A further preferred embodiment is directed towards a digital signal analysis method for distinguishing and characterizing the properties of high-gamma (65-250 Hz) and beta (14-30 Hz) oscillation biomarkers in electrical signals recorded from left BA40 during wakefulness and transforming these values in to a measurement of human memory performance. The invention consists of a signal processing method that is executed as computer code in the programming language Matlab (Natick, MA) (or other suitable language). High-gamma oscillations are typically long lasting (100+ msec) oscillatory activity with a frequency content between (65-250 Hz). High gamma oscillations are unique because increased high-gamma power correlates with both increased action potential firing of neurons, and increased BOLD signal on fMRI (Mukamel et al., 2005). Beta oscillations are typically longer lasting as compared to high-gamma oscillations and range in spectral content between (14-30 Hz). The properties of distinct high-gamma and beta oscillations during encoding and recall include onset, offset, spectral content, power, and duration. In left BA40 these properties of the high-gamma and beta oscillation biomarkers that occur during memory encoding and recall can be used to classify human memory performance. Distinguishing and characterizing high-gamma and beta oscillations in electrical signals of brain activity can be accomplished using the technique of the topographical analysis of the wavelet convolution. Machine learning algorithms such as logistic regression, or deep or shallow neural networks can be utilized to transform the properties of the high-gamma (65-250 Hz) and beta (14-30 Hz) oscillation cognitive biomarkers measured in left BA40 during wakefulness in to a measurement of human memory performance.

A further embodiment of the invention is directed towards a digital signal analysis method for distinguishing and characterizing the properties of high-gamma (65-250 Hz) and beta (14-30 Hz) oscillation biomarkers in electrical signals recorded from left BA40 during wakefulness and transforming these values into a measurement of human memory performance, and triggering distinct regimens of environmental, digital, or brain stimulation based on the magnitude of the measurement of human memory performance comprising: a computer processor; and a non-transitory computer-readable memory storing instructions executable by the computer processor; a digital output; and wherein said instructions, when executed by the computer processor, perform steps comprising: applying wavelet convolutions to the electrical signals to generate a time-frequency representations; determining a region or regions of the time-frequency plot that corresponds with high-gamma band oscillations on the basis of a predetermined threshold; characterizing the properties of high-gamma band oscillations including, onset, offset, power, duration, and spectral content using a topographical analysis of the wavelet convolution; determining a region or regions of the time-frequency plot that corresponds with beta band oscillations on the basis of a predetermined threshold; characterizing the properties of beta band oscillations including, onset, offset, power, duration, and spectral content using a topographical analysis of the wavelet convolution; determining the properties including onset, offset, power, duration, and spectral content of all high-gamma and beta band oscillations during a predetermined epoch of electrical signals recorded from a plurality of electrodes; and classifying the subject's memory performance on the basis of a comparison of these oscillations' properties with the subject's prior human memory performance and the properties of the corresponding oscillations; and generating a report of the subject's current and past memory performance and the properties of the corresponding oscillations.

A further embodiment is directed towards a method of use of a device composed of a) embedding into a subject at least one electrode; b) a brain signal acquisition device to record electrical signals from left BA40 c) a non-transitory computer-readable memory storing instructions executable by the computer processor; d) a computer processor; and e) generating digital outputs that transmit the report of human memory performance derived using the signal processing method to other computers located outside the patient or implanted within the patient.

A further embodiment is directed towards using a device composed of a) embedding into a subject a plurality of electrodes; b) a brain signal acquisition device connected to said electrodes to record electrical signals from left BA40 c) a non-transitory computer-readable memory storing instructions executable by the computer processor; d) a computer processor; e) digital outputs; f) a multichannel stimulator; wherein, g) within the subject with a plurality of brain stimulating electrode(s), utilizing a report defined by signals received in the left BA40 to determine when memory encoding performance is strong or weak, or when memory recall performance is strong or weak the device can stimulate brain region(s) with therapeutic regimens to enhance memory. In certain embodiments, the method may comprise detecting a baseline parameter for said patient and comparing the report generated from baseline to a second time, wherein the comparison quantifies memory encoding performance.

A method of determining the level of memory encoding performance in a patient comprising: a) embedding into a subject at least one electrode, said electrode connected to a brain signal acquisition device to record electrical signals from left BA40 and comprising a non-transitory computer-readable memory storing instructions executable a computer processor; b) providing a stimulus to said patient; c) recording the electrical signals from left BA40; and d) generating digital outputs that transmit the report of human memory performance derived using the signal processing method to other computers located outside the patient or implanted within the patient.

In a preferred embodiment, a system for assessing memory health of a patient comprising: capturing electrical signals from the left BA 40 for the high-gamma (65-250 Hz) and beta (14-30) oscillations while displaying an image to a patient to capture the electrical signals during image/memory encoding; and capturing electrical signals from the left BA 40 for the high-gamma and beta during memory recall, when the patient is asked to recall the images displayed to said patient; filtering said signals for the high-gamma and beta oscillations; determining accuracy of the response; and comparing the beta and high-gamma oscillations to a control data set; quantify the beta and high-gamma oscillations as compared to the accuracy and generating a quantifiable score of memory based upon said comparison. In certain embodiments, the image is a standardized neurophysiological assessment.

In a preferred embodiment, a method of capturing biomarker data from a patient to assess memory performance comprising: a) embedding into a subject at least one electrode, said electrode connected to a brain signal acquisition device to record electrical signals from left BA40 and comprising a non-transitory computer-readable memory storing instructions executable a computer processor; b) providing a stimulus to said patient; c) recording the electrical signals from left BA40 in the beta and high-gamma oscillations; and d) generating digital outputs that transmit the report of human memory performance derived using the signal processing method to other computers located outside the patient or implanted within the patient.

In a preferred embodiment, a method for monitoring human memory performance in a subject by recording electroencephalographic activity from the left Brodmann Area 40 (BA40) using an electrical sensing device consisting of at least one electrode and using one or more processors to:

detecting and capturing electrical signals from the left BA40 using the electrical sensing device; applying wavelet convolutions to the captured electrical signals to generate a time-frequency representation using Morlet wavelets method with a wavelet width of 20 for high gamma (65-250 Hz), and 10 for beta band (14-30 Hz); determining a region or regions of the time-frequency plot that corresponds with high-gamma band oscillations on the basis of a predetermined threshold of $1*10^7$ arbitrary units or equivalent; characterizing the properties of high-gamma band oscillations including, onset, offset, power, duration, and spectral content using a topographical analysis of the wavelet convolution; determining a region or regions of the time-frequency plot that corresponds with beta band oscillations on the basis of a predetermined threshold; characterizing the properties of beta band oscillations including, onset, offset, power, duration, and spectral content using a topographical analysis of the wavelet convolution; determining the properties including onset, offset, power, duration, and spectral content of all high-gamma and beta band oscillations during a predetermined epoch of electrical signals recorded from a plurality of electrodes; and classifying the subject's memory performance on the basis of a comparison of these oscillations' properties with a prior human memory performance from the subject and the properties of the corresponding oscillations; and generating a report of the subject's current and past memory performance and the properties of the corresponding oscillations.

In a further preferred embodiment, the method wherein the electrical sensing device is a non-invasive or minimally invasive electroencephalogram.

In a further preferred embodiment, the method wherein the electrical sensing device is an intracranial electroencephalogram.

In a preferred embodiment, a system for monitoring human memory performance by recording electroencephalographic activity from the left Brodmann Area 40, said system comprising: a data acquisition device for receiving an electrical signal sensing device configured to record electrical signals from multiple locations of a patient's left Brodmann Area 40; a memory storage system for storing instructions; and a microprocessor communicatively coupled to the memory storage system, the microprocessor being configured to execute instructions stored in the memory storage system to cause the system to: record, using the electrical signal sensing device, electrical signals from multiple locations in the left Brodmann Area 40 of a subject; applying wavelet convolutions to the electrical signals to generate a time-frequency representation; determining a region or regions of the time-frequency plot that corresponds with high-gamma band oscillations on the basis of a predetermined threshold; characterizing the properties of high-gamma band oscillations including, onset, offset, power, duration, and spectral content using a topographical analysis of the wavelet convolution; determining a region or regions of the time-frequency plot that corresponds with beta band oscillations on the basis of a predetermined threshold; characterizing the properties of beta band oscillations including, onset, offset, power, duration, and spectral content using a topographical analysis of the wavelet convolution; determining the properties including onset, offset, power, duration, and spectral content of all high-gamma and beta band oscillations during a predetermined epoch of electrical signals recorded from a plurality of electrodes; and classifying the subject's memory performance on the basis of a comparison of these oscillations' properties with a prior human memory performance of the subject and the properties of the oscillations corresponding to the past memory performance; and generating a report of the subject's current and past memory performance and the properties of the corresponding oscillations for the determination of the parameters for a therapeutic procedure for improving human memory performance.

In a further preferred embodiment, the system, wherein the electrical signal sending device comprises an implantable or wearable device.

In a further preferred embodiment, the system, further comprising implanting a therapeutic device in the subject, and using the therapeutic device to administer, without user intervention, the therapy in response to the report of electrical signals at identified locations in left Brodmann Area 40 displaying high-gamma and beta oscillations of a predefined onset, offset, power, duration, and spectral content In a further preferred embodiment, the system, wherein the microprocessor is further configured to execute instructions stored in memory storage system to cause the system to use the therapeutic device to administer, without user intervention, a therapy at a predetermined location.

In a further preferred embodiment, the system, wherein the therapy is electrical or electromagnetic stimulation In a further preferred embodiment, the system, wherein the therapy is optogenetic stimulation In a further preferred embodiment, the system, wherein the therapeutic device administers, without user intervention environmental stimuli such as an audio alert in response to left Brodmann Area 40 displaying high-gamma and beta oscillations of a predefined onset, offset, power, duration, and spectral content.

In a further preferred embodiment, the system, wherein a prior human memory performance comprises use of the same system, under the same protocol, at a prior time.

In a further embodiment, a system for detecting and characterizing memory performance comprising: a non-transitory computer readable medium storing instructions that, when executed by a processor, are configured to identify brain electrical activity displaying of a predefined high-gamma and beta oscillations of a predefined onset, offset, power, duration, and spectral content were recorded by: receiving electrical signals recorded from multiple locations in the left Brodmann Area 40 of a subject using an electrical signal sensing device;

a memory storage system for storing instructions; and a microprocessor communicatively coupled to the memory storage system, the microprocessor being configured to execute instructions stored in the memory storage system to cause the system to: record, using the electrical signal sensing device, electrical signals from multiple locations in the left Brodmann Area 40 of a subject; applying wavelet convolutions to the electrical signals to generate a time-frequency representation; determining a region or regions of the time-frequency plot that corresponds with high-gamma band oscillations on the basis of a predetermined threshold; characterizing the properties of high-gamma band oscillations including, onset, offset, power, duration, and spectral content using a topographical analysis of the wavelet convolution. determining a region or regions of the time-frequency plot that corresponds with beta band oscillations on the basis of a predetermined threshold; characterizing the properties of beta band oscillations including, onset, offset, power, duration, and spectral content using a topographical analysis of the wavelet convolution; determining the properties including onset, offset, power, duration, and spectral content of all high-gamma and beta band oscillations during a predetermined epoch of electrical signals recorded from a plurality of electrodes; and classifying the subject's memory performance on the basis of a comparison of these oscillations' properties with the prior human memory performance of the subject and the properties of the oscillations corresponding to the past memory performance; and generating a report of the subject's current and past memory performance and the properties of the corresponding oscillations for the determination of the parameters for a therapeutic procedure for improving human memory performance.

A method for detecting and quantifying the level of memory encoding comprising: collecting data from the left BA 40 from a patient at a first time; classifying memory status by evaluating high gamma and beta biomarkers from said data; measuring the memory performance of a patient based on the quantification of high gamma and beta biomarkers; collecting data from the left BA 40 from said patient at a second time; and comparing the high gamma and beta biomarkers between the first time and the second time.

In a further embodiment, the method, wherein the beta oscillations are defines as those between 14-30 Hz and detected within a predefined temporal interval using the topographical analysis of the wavelet convolution at each of these locations in left BA40.

In a further embodiment, the method, wherein the high gamma oscillations are defined as those between 65-240 Hz and detected within a predefined temporal interval using the topographical analysis of the wavelet convolution at each of these locations in left BA40.

A method for detecting and quantifying the level of memory recall comprising: collecting data from the left BA 40 from a patient at a first time; classifying memory status by evaluating high gamma and beta biomarkers from said data; measuring the memory performance of a patient based on the quantification of high gamma and beta biomarkers; collecting data from the left BA 40 from said patient at a second time; and comparing the high gamma and beta biomarkers between the first time and the second time. In a further embodiment, the method wherein the beta oscillations are defines as those between 14-30 Hz and detected within a predefined temporal interval using the topographical analysis of the wavelet convolution at each of these locations in left BA40. In a further embodiment, the method, wherein the high gamma oscillations are defined as those between 65-240 Hz and detected within a predefined temporal interval using the topographical analysis of the wavelet convolution at each of these locations in left BA40.

In a preferred embodiment, a method for determining human memory performance comprising: collecting data from the left BA 40 from a patient at a first time; classifying whether the subject's data is encoding, recalling, or performing another cognitive task; classifying memory status by evaluating high gamma and beta biomarkers from said data; measuring the memory performance of a patient based on the quantification of high gamma and beta biomarkers; collecting data from the left BA 40 from said patient at a second time; and comparing the high gamma and beta biomarkers between the first time and the second time. In a further preferred embodiment, the method wherein the beta oscillations are defines as those between 14-30 Hz and detected within a predefined temporal interval using the topographical analysis of the wavelet convolution at each of these locations in left BA40. In a further preferred embodiment, the method, wherein the high gamma oscillations are defined as those between 65-240 Hz and detected within a predefined temporal interval using the topographical analysis of the wavelet convolution at each of these locations in left BA40.

A further embodiment is directed towards a method for diagnosing memory loss in a patient comprising: creating a library of high gamma and beta oscillations that correspond to quantified measurements of memory performance created during a standardized neuropsychological assessment with neurophysiological recording; obtaining data from a patient from the left BA 40 and collecting the high gamma and beta oscillations from said patient while performing said standardized neuropsychological assessment with neurophysiological recording; comparing the high gamma and beta oscillations between said library and said patient.

In a further preferred embodiment, the method further comprising determining a level of memory loss by determining the amount of difference between the library and said patient.

In a further preferred embodiment, the method wherein the library comprises a patient population of the same gender and within five years of age of the patient; wherein memory loss is generated as a relational number by comparison to the library of patient population. In a further preferred embodiment, the method wherein the relational number is between 0 and 100. In a further preferred embodiment, the method wherein the relational number is generated as a standard deviation from a bell-curve plot of the library. In a further preferred embodiment, the method wherein the beta oscillations are defines as those between 14-30 Hz and detected within a predefined temporal interval using the topographical analysis of the wavelet convolution at each of these locations in left BA40. In a further preferred embodiment, the method wherein the high gamma oscillations are defined as those between 65-240 Hz and detected within a predefined temporal interval using the topographical analysis of the wavelet convolution at each of these locations in left BA40.

In a preferred embodiment, a method of assessing status of memory of a patient comprising: creating a library of high gamma and beta oscillations that correspond to quantified measurements of memory performance created during a standardized neuropsychological assessment with neurophysiological recording; obtain data from a patient from the left BA40 and collect the high gamma and beta oscillations while performing said standardized neuropsychological assessment with neurophysiological recording; comparing the high gamma and beta oscillations between said library and said patient.

In a preferred embodiment, the method, wherein the library comprises a patient population of the same gender and within five years of age of the patient; wherein the measure of memory loss is generated as a relational number by comparison to the library of patient population.

In a preferred embodiment, the method, wherein the relational number is between 0 and 100.

In a preferred embodiment, the method, wherein the relational number is generated as a standard deviation from a bell-curve plot of the library.

In a preferred embodiment, the method, wherein the beta oscillations are defined as those between 14-30 Hz and detected within a predefined temporal interval using the topographical analysis of the wavelet convolution at each of these locations in left BA40.

In a preferred embodiment, the method, wherein the high gamma oscillations are defined as those between 65-240 Hz and detected within a predefined temporal interval using the topographical analysis of the wavelet convolution at each of these locations in left BA40.

In a preferred embodiment, the method further comprising: monitoring an individual's memory performance over a predetermined set of time; and generating a continuous report of the individual's memory workload and memory state.

In a preferred embodiment, the method, further comprising wherein the continuous report is utilized for judging and predicting educational or occupational performance.

In a preferred embodiment, the method further comprising wherein the continuous report is utilized for the diagnosis of neurological and psychiatric ailments such as memory disorders.

In a preferred embodiment, the method further comprising wherein the continuous report is utilized to determine efficacy of a therapeutic compound; wherein the report can be used to determine if the therapeutic compound significantly modified memory performance over time.

A method of improving memory in a patient comprising: detecting high gamma and beta oscillations from the left BA 40 in said patient; generating a baseline data for high gamma and beta oscillations for said patient comprising performing a standardized neuropsychological assessment with neurophysiological recording and obtaining data regarding high gamma and beta oscillations during encoding and recall processing; applying an electrical stimulus to said patient to modify the high gamma and beta oscillations in the left BA 40 when the high gamma and beta oscillations are more than two standard deviations from the baseline.

In a preferred embodiment, the method wherein the applying step of an electrical stimulus is applied when the high gamma and beta oscillations are more than one standard deviation from the baseline. In a preferred embodiment, the method, wherein the beta oscillations are defined as those between 14-30 Hz and detected within a predefined temporal interval using the topographical analysis of the wavelet convolution at each of these locations in left BA40. In a preferred embodiment, the method, wherein the high gamma oscillations are defined as those between 65-240 Hz and detected within a predefined temporal interval using the topographical analysis of the wavelet convolution at each of these locations in left BA40.

A device composed of a) a plurality of electrodes capable of detecting oscillations in the brain of a subject 10; b) a brain signal acquisition device (Amplifier/digitizer) 11 to record electrical signals from multiple locations of a subject; c) a non-transitory computer-readable memory storing instructions executable 12 by the computer processor 13; d) a computer processor 13; e) digital outputs 14; f) a multichannel stimulator 15; wherein the computer processor; and a non-transitory computer-readable memory storing instructions executable by the computer processor; are configured to execute the method applied to the brain signals recorded by the plurality of the electrodes, for example include the RAM, BIOS, an operating system, application programs, program data, and other program modules as necessary to implement and run the system; and wherein the report generated by the method is translated by the computer processor and computer-readable memory in to a train of TTL pulses transmitted by the digital output; and wherein said multichannel stimulator, operably connected to the digital output reads the TTL pulses and electrically stimulates the brain by generating current that is transmitted via the brain stimulating electrode.

BRIEF DESCRIPTION OF THE DRAWINGS

FIG. 1 depicts the change in the probability of human memory recall, and the significance of this change, when a spike (n=) or ripple (n=) oscillation occurs in a given brain area during memory encoding.

FIG. 2 depicts the change in the probability of human memory recall, and the significance of this change, when a spike (n=) or ripple (n=) oscillation occurs in a given brain area during memory encoding.

FIG. 3 depicts the change in the probability of human memory recall, and the significance of this change, when a spike (n=) or ripple (n=) oscillation occurs in a given brain area during memory encoding.

FIG. 4 depicts a characteristics of the patient's with electrodes implanted in left Brodmann area 40.

FIG. 11 depicts the area under the receiver operating characteristic curve from logistic regression classifier of recall success using left BA40 high-gamma and beta oscillation biomarkers during encoding.

FIG. 14 depicts the statistically significant linear correlation between high-gamma power measured from left BA40 during the recall epoch and the number of words recalled.

FIG. 16 depicts the statistically significant linear correlation between beta (14-30 Hz) power measured from left BA40 during the recall epoch and the number of words recalled.

DETAILED DESCRIPTION OF THE PREFERRED EMBODIMENTS

Figure 5:
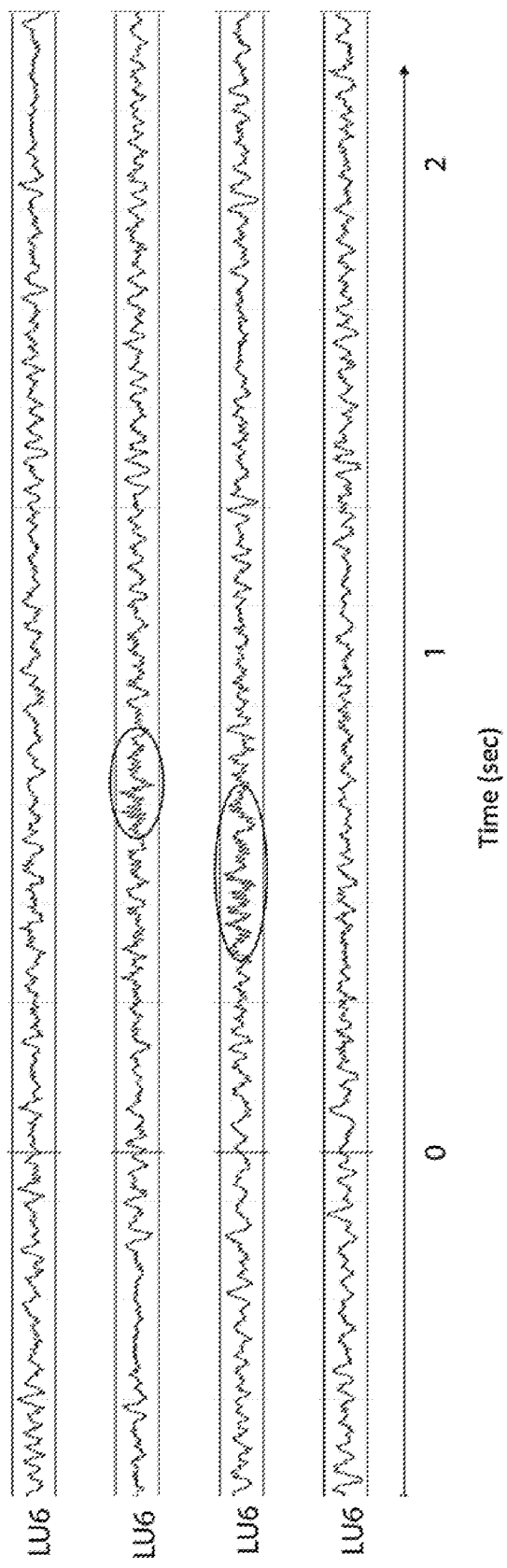
FIG. 5 depicts an example intracranial EEG recordings from left Brodmann area 40 showing memory encoding high-gamma biomarker.

It is estimated that approximately 20% of people over the age of 70 have mild cognitive impairment. Cognitive impairment and dementia also affects over 1% of individuals under 40. Worsening episodic and working memory is a common clinical symptom of mild cognitive impairment. Working memory is defined as short-term memory that is concerned with immediate conscious perceptual and linguistic processing. Episodic memory is the memory of autobiographical events (times, place, associated emotions, and other contextual who, what, when, where, why knowledge that can be explicitly stated or conjured.

Clinical strategies to improve working and episodic memory have focused on pharmacological and surgical intervention. One potential surgical intervention is implanting a deep brain stimulating (DBS) electrode in to a predetermined region of the brain which can record naturally generated electrical activity. Another is noninvasive deep brain stimulation via temporally interfering electrical fields (Grossman et al., 2017). At appropriate instances, both can act as a conduit for electrical impulses generated by a stimulator to reach the desired brain region thereby stimulating or inhibiting populations of neurons. Closed-loop stimulation refers to recording brain activity for the purpose of triggering an appropriate protocol of stimulation to achieve the desired effect. Open-loop stimulation refers to the activation of a stimulation protocol in the absence of a brain signal trigger to achieve a desired effect.

Identifying the neuroanatomical sites in which electrical stimulation of the brain results in an efficacious improvement in working or episodic memory presents challenges. In patients with epilepsy, electrical stimulation of specific regions of the hippocampal formation has been shown to enhance episodic memory (US20140107728A1).

However, these results have not been replicated in subsequent experiments. It is technically challenging to conduct large clinical trials that systematically investigate whether episodic and/or working memory can be improved by brain stimulation of a specific neuroanatomical structure. Therefore, it is very difficult to identify which neuroanatomical location(s) would be best suited for this purpose. Certain prior studies have indicated that the Left middle temporal gyms is the most sensitive to applied stimulation (Ezzyat et al., 2018; WO2018017655A1).

However, the effects include only a mild verbal episodic memory improvements. Accordingly, while it may have benefits to some, it will not affect all.

Herein, we describe a novel technology which is a system for measuring human memory performance through quantifying biomarkers of memory performance. This technology would have many applications in medicine and society. By monitoring an individual's memory performance the system could generate a continuous report of the individual's memory workload and memory state that could be reviewed by the individual or others on a continuous basis. The results from this report could be utilized for judging and predicting educational or occupational performance. The results could also be used for the diagnosis of neurological and psychiatric ailments such as memory disorders. In the case of a trial of a pharmaceutical compound the report can be used to determine if the study drug significantly modified memory performance over time. Although neuropsychological testing is suitable for many of these applications, neuropsychological testing cannot provide a continuous report of performance over days, months, or years. Continuous testing will provide a more accurate measurement since individuals experience alternating periods of emotional states, attention states, stress, and performance.

A system for measuring human memory performance using a memory biomarker has utility beyond diagnostic applications. The continuous report of the individual's memory performance can be used as an input for a cognitive brain-computer interface with applications to improve human memory, or control applications on a computer. The continuous report of the individual's memory performance can also be used as a signal for use by the monitored individual as biofeedback to improve his/her memory performance.

Perhaps the most important application of a system for human memory performance monitoring using a memory biomarker is that the continuous report of the individual's memory performance can be used to control the strength, site, timing, or other parameters of brain stimulation. This form of closed-loop brain stimulation may be useful to improve memory function for individuals who experience memory disorders (Ezzyat et al., 2018). Currently, only acetylcholinesterase inhibitors and NMDA receptor antagonists show mild efficacy in improving memory function in individuals with memory disorders. Closed loop brain stimulation is currently being investigated as another means for improving memory in affected individuals.

Indeed, herein we describe that high-gamma (65-250 Hz) and beta (14-30 Hz) band oscillations in left Brodmann area 40 (BA40) of the left cerebral hemisphere are a newly identified biomarker of memory performance during memory encoding and recall. BA40 is located within the inferior parietal lobule, which is located within the posterior parietal cortex (PPC). Prior research has already implicated the PPC in mediating memory encoding and recall, but none have identified the left BA40 for its specific implications and ability to identify memory function. Functional MRI has been used to demonstrate that in the ventral PPC (vPPC) during memory encoding, content selectivity of the region positively associated with memory recall, even as both measures were negatively associated with BOLD activation (Lee et al., 2017). A role for the PPC in memory retrieval was also shown by demonstrating that single neuron responses in the PPC encode memory confidence and stimuli familiarity (Rutishauser et al., 2018). High-gamma and beta oscillations have already been shown to be important in memory. High-gamma oscillations in the intracranial EEG recorded from the PPC are increased in strength during correct recall as opposed to failed recall i.e. forgetting (Gonzalez et al., 2015). Whereas, in the primate frontal lobe high-gamma and beta oscillations have been found to be a read out signal of working memory (Lundqvist et al., 2016). While this prior work has suggested that gamma and beta oscillations in areas near left BA40 are involved in memory encoding and recall, hitherto no published work has utilized these signals as a biomarker that could be used to monitor human memory performance by classifying strong vs. weak memory encoding states, and strong vs. weak memory recall states as is described herein.

With the new found understanding that high gamma (65-250 Hz) and beta (14-30 Hz) band oscillations in left BA40 can serve as biomarkers of memory performance, a system and device that monitors human memory performance by quantifying these biomarkers was developed. The applications of this system include established uses such as assessing an individual's educational, or occupational fitness, and/or diagnosing a neurological or psychiatric condition. Other applications of this system are novel such as use in a cognitive brain-computer interface, biofeedback, or closed loop brain stimulation.

Heretofore, an electrophysiological biomarker of human memory performance has not yet been reported. Herein, we demonstrate that high-gamma (65-250 Hz) and beta (14-30 Hz) band oscillations generated in left Brodmann Area 40 (BA40) satisfy the most basic criteria for biomarkers of human memory performance. A biomarker of memory performance should exhibit altered expression in healthy regions depending on the efficacy of memory encoding and/or recall. We identified high-gamma (65-250 Hz) and beta (14-30 Hz) band oscillations generated in left BA40 as a candidate biomarker of human performance using a unique data mining approach applied to a library of digital intracranial EEG recordings performed in epilepsy patients during a word list-learning task (Ezzyat et al., 2018). After identifying the candidate biomarkers and the location of the expression of the candidate biomarkers, we determined that the expression of the biomarkers in left BA40 significantly correlated with memory performance in each subject. Next, we utilized a logistic regression model trained using left BA40 high-gamma and beta oscillation(s) properties (onset, offset, power, duration, and spectral content) during word encoding to predict recall performance. We tested this trained logistic regression model on a distinct set of word encoding trials to predict the probability of recall to provide proof of principle that high-gamma and beta oscillations in left BA40 are biomarkers of human memory performance. We also asked if the human memory performance measurement derived from the biomarkers influenced the effect of brain stimulation on memory performance.

Subjects:

The initial data pool consisted of task data from 275 subjects undergoing intracranial EEG (iEEG) monitoring for intractable epilepsy. Data were collected as part of the multi-site DARPA (Defense Advanced Research Projects Agency)-funded "Restoring Active Memory" project, from sites including: Columbia University Medical Center (New York, NY), Dartmouth-Hitchcock Medical Center (Lebanon, NH), Emory University Hospital (Atlanta, GA), Hospital of the University of Pennsylvania (Philadelphia, PA), Mayo Clinic (Rochester, MN), National Institute of Neurological Disorders and Stroke (Bethesda, MD), Thomas Jefferson University Hospital (Philadelphia, PA), University Texas Southwestern Medical Center (Dallas, TX), and Washington University Medical Center (St. Louis, MO). The study was coordinated by the University of Pennsylvania and approved by each respective IRB, with informed consent obtained from each subject.

From this pool, 181 patients were selected for memory performance biomarker screening. Also, from the pool of 275 subjects, electrode contacts were chosen from left Brodmann area 40 which were not in the seizure onset zone and which did not contain any interictal spikes in their recordings, as determined by expert clinicians. The remaining data consisted of 281 subject-task-electrode combinations from 35 distinct subjects (16 male, 15 female; ages 19-64, mean+−s.d.=37±12).

Data Acquisition:

Neurophysiological Recording:

Data consists of iEEG recordings from depth, strip, and grid electrodes (AdTech Inc., PMT Inc.) implanted based on patient-specific clinical demands. iEEG data were collected using Nihon Kohden® EEG-1200, Natus XLTek® EMU 128, or Grass® Aura-LTM64, depending on the specific site at which data was collected. IEEG signals were referenced to a common intracranial, scalp, or mastoid contact, and bipolar montages were then calculated from the subtraction of adjacent electrodes. The resulting bipolar electrodes served as the electrodes subsequently analyzed in this study. Sampling rate ranged from 500 to 2000 Hz depending on site. All channels were visually inspected for epileptic activity, low signal-to-noise, and artifact, and discarded from analysis accordingly.

Prior to electrode implantation T1-weighted MRIs were obtained for each individual. Post-implantation CT scans were co-registered with the pre-implantation MRIs using ANTS (Avants et al, 2008) and neuroradiologist supervision. These images were then transformed into standard MNI and Talairach coordinates in order to identify the electrode coordinates in standard space. Brodmann areas were additionally identified for each electrode contact, based on these localizations. Only electrode contacts from left Brodmann area 40 were used in this study.

Behavioral Task:

To examine memory function we used a delayed verbal free recall task, which targets memory processing underlying episodic memory, similar to other tasks shown to be reliable indicators of memory impairments. Experimental sessions consisted of 12 word presentations ("trials") per block, with 25 blocks per session. Patients performed variable numbers of sessions. Words were presented visually on screen for 1.6 seconds, followed by a random variable interval of 0.75-1 seconds. After the block of 12 words, an arithmetic distractor task was administered for 20 seconds. Finally, the patient had 30 seconds to recall as many words as possible during the recall phase. A second version of the task was also used, which was identical in all respects except that the 12 words in a given block were chosen from the same random category.

The data segments used for analysis here consisted of the 300 ms preceding stimulus presentation up to the 1.7 seconds following stimulus onset from the encoding epoch, as well as the distractor period, which was used as a control for some subsequent analyses. We also analyzed the complete recall epoch for a select set of recordings.

Detecting Candidate Ripple Events in iEEG Recordings

Prior to data preprocessing, we first determined which depth electrode iEEG recordings exhibited a signal to noise ratio sufficient for accurate ripple detection. Brain surface electrocorticography recordings were not included in this study because these recordings frequently exhibited insufficient signal to noise ratios. iEEG recordings were bandpass filtered (80-240 Hz) using a finite impulse response filter. The filter order was set to be ⅓ of the number of data points in the trial, to maximize the filter order for the calculation. For each electrode contact recording we calculated the root mean square (RMS) value during each encoding word trial. We took the mean of this RMS value and excluded electrode contacts exceeding between 1.5-1.8 µV depending on the amplifier make used to acquire the data.

Following the exclusion of recordings from electrode contacts with excessive high frequency artifacts we selected the time intervals of the recordings that would be subject to our analysis. During encoding, the jitter between each word trial varied between 750-1000 msec.

Due to this variability we selected for our analysis of the word encoding trial iEEG recordings which concatenated the final 750 msec of pre-word interval with the 1600 msec of word presentation. For the distractor and recall epochs we divided the entire recording period into 2000 msec contiguous trials. We next generated a time-frequency (TF) plot of each trial using wavelet convolution in the time domain. Complex Morlet wavelets were created with constant frequency domain width $f\_o/\sigma\_f=7$, where $f\_o$ is the wavelet central frequency and $\sigma\_f$ is the standard deviation of its Gaussian envelope in the frequency domain. The central frequency, and its standard deviation of the Gaussian envelope values were frequency dependent and varied between the lower and upper limits (50-240 Hz) of the TF analysis. Prior to performing the wavelet convolution, the digital recording of the iEEG were padded with zeros until the sample count was equal to the closest power of two greater than the initial number of samples. The time frequency plot was not normalized. Ripple events occur within a range of 80-200 Hz. Due to boundary effects caused by continuous wavelet convolution of finite length signals, a range of 50-240 Hz was selected for the time-frequency (TF) plot in order to buffer the frequency range of interest, then frequencies below 80 Hz were discarded. To further reduce boundary effects, we also discarded the initial and final 70 msec of the time-frequency (TF) plot.

To identify the candidate ripple events (ripple on spike [RonS] and ripple on oscillation [RonO]) in the time-frequency plot we used a power magnitude threshold of $1*10^7$ arbitrary units. This power threshold corresponds to a ripple with a peak amplitude of approximately 8 μN. We chose this threshold to define only those events with good inter-rater reliability upon visual inspection. Detected ripple on oscillation events were inspected and edited in Brainquick™ (Micromed S.p.A., Treviso, IT).

When the TF plots of an iEEG trial did not exhibit a power magnitude maximum meeting this threshold it was denoted as a null event. For trials with sufficient power magnitudes, the time and frequency coordinates±150 msec corresponding to the maximum power magnitude were considered as the candidate event epoch, but not the event itself. The candidate event epoch was subsequently processed using the topographical analysis to define the event and when appropriate the power, duration, and frequency of the event. We did not seek to characterize multiple events in single trials, but rather only the event of largest spectral power.

Classifying and Characterizing Ripple Events in iEEG Trials Using Topographical Analysis To determine whether the candidate ripple event was a true ripple or a result of filter ringing from a sharply contoured spike or artifact, we applied a topographical analysis to the time-frequency (TF) plot. To develop an automatic software method for classifying ripples as true or false, we utilized the difference in the time-frequency (TF) representation of sharp transients and true high frequency oscillations. Time-frequency plots of time series data exhibit an inherent topography defined by isopower contours. A true ripple is represented by a "blob" of power within the ripple band (80-250 Hz), and if contour lines are defined for a TF representation of the "blob", with the maximum and minimum frequencies confined to the ripple band, the contours will have closed loops. In contrast, a false ripple is represented by a "candle" of power in the ripple band, but importantly this "candle" continues below the ripple band. Thus, when the contour lines are defined for the "candle" within the ripple band, the contours will have open loops. This same method was used to derive the mean spectral content, duration, and power of each ripple event. For this signal processing method, we selected the portion of the TF plot centered around the candidate ripple event ±150 ms. The topographical analysis was performed by calculating a contour map of this portion of the TF plot, consisting of 50 contours of isopower. The 50 contour levels were evenly spaced between, and including, the minimum and maximum power magnitude of the TF plot. Each contour consisted of its isopower magnitude level and the TF coordinates of its vertices.

To differentiate true from false ripple on spike events, all contours corresponding to levels below the power magnitude threshold of $1*10^7$ arbitrary units were removed. Each of the remaining contours was subsequently classified as a closed-loop contour (CLC) or open-loop contour (OLC) group based on whether its first and last vertex coordinate were identical. CLCs surrounded or surrounding other CLCs were grouped together. For a group of CLCs, if the inner contours were at a lower power level than the outer contours, the group was identified as a valley and removed from consideration. Groups containing fewer than 3 CLCs were categorized as 'lone contour groups' and also removed from consideration. Of the remaining CLC groups, the group with the maximum power magnitude is identified as a true ripple event. In the absence of CLC groups, OLCs above the threshold were identified as a potential false ripple i.e. sharply contoured spike.

Quantification of Ripple Spectral Content and Power.

In the case of a true ripple detection, for the CLC group identified as the ripple event, the CLC at the lowest power level is selected as the event boundary contour 'B'. The region of the TF map encircled by the boundary B are used to quantify three properties of the ripple event: the average power magnitude, the power-weighted mean frequency, and the duration of each true ripple event. The average power magnitude of the ripple is determined by calculating the mean power magnitude across all TF coordinate points of the TF map within boundary B. The magnitude-weighted mean frequency of the ripple event was calculated using:

$$\overline{f_{hfo}} = \sum_i^B \frac{f_i * P_i}{\sum P_i} \qquad \text{eqn. 1}$$

where fi and Pi and are the frequency and power amplitude of the coordinate of the TF map within the boundary contour, B. Finally, the duration of the ripple event is calculated as the difference between the minimum and maximum time coordinate associated with the vertices of the boundary B.

Identification of Superimposed Interictal Discharges in the iEEG Using a Topographical Analysis of Time-Frequency Plots.

Sharply contoured epileptiform spikes produce a motif on time-frequency spectrograms related to the waveform morphology and not the amplitude of the event. The novel detector sought to identify this motif by using a topographical analysis of the TF plot that identified and characterized distinct elevations in both the power, and the gradient of the power, in TF space. These elevations represent objects and we hypothesized that objects that met certain criteria would always correspond with interictal epileptiform spike events.

We identified these candidate events by first creating objects by thresholding the TF plot and its gradient to values >20% of the maximum. After applying this threshold it was possible to define the borders of the objects in the resulting TF plot, and its gradient, by using this same threshold to derive a binary map. We subsequently calculated the volume of each object, within its defined boundaries, using a trapezoidal surface integration for each of the objects. To determine if any of the identified and characterized objects were representative of interictal epileptiform spikes we applied separate thresholds to the derived volumes for the objects in the TF plot and its gradient.

Specifically, the iEEG trials were processed using a real Morlet-based wavelet convolution to compute the TF map. The wavelets were created with constant frequency domain width f_o/σ_f=6, to better distinguish shapes associated with spikes in the TF plot from background activity. We analyzed the portion of the resulting TF plot centered around the detected ripple event ±200 ms. We derived a gradient plot of the TF plot by calculating both the horizontal gradient of the TF plot $\nabla P\_t=(\partial(\text{power magnitude}))/(\partial(\text{time}))$ and the vertical gradient of the TF plot $\nabla P\_f=(\partial$ (power magnitude))/(∂(frequency)) and combining these two gradients as $\nabla[\![TF]\!]\_map = \sqrt{([\![(\nabla P\_f)]\!])^2 + [\![(\nabla P\_t)]\!]^2)}$.

To define the thresholds for both the TF plot and its gradient used to define the object boundaries we used 20% of the respective maximum values. Following binarization of the maps using this threshold we identified the boundary coordinates of each object using a Moore-neighbor tracing algorithm modified by Jacob's stopping criteria. We then determined the volume of each object within its boundaries by approximating the surface integral using trapezoidal numerical integration.

To identify the objects that corresponded to interictal epileptiform spikes, we first identified the object with the greatest power maximum value. We then determined if the volume of this object met a predetermined threshold and if in the gradient plot corresponding objects also met a predetermined threshold. The correspondence of the object in the time-frequency plot and the objects in the gradient plot was confirmed by measuring the distance between the centroids of these objects. Due to edge effect we excluded objects in the TF plot that had a power maximum value near the TF plot borders. We also excluded objects that had a height-width ratio less than 0.7, because these objects more often represented bursts of gamma oscillations.

By classifying and characterizing ripple events in iEEG trials, and identifying superimposed interictal discharges in the iEEG using the topographical analysis of time-frequency plots, we could classify each event as either 1) a ripple on spike (i.e. RonS), 2) a ripple that does not occur on a spike, but rather occurs on background EEG oscillations (i.e. RonO), or 3) a sharply contoured epileptiform spike that generates a ripple due to filter ringing (i.e. Spike).

Naïve Bayesian Machine Learning—Conditional Probability Model

To examine the effects of spikes and ripples on encoding, predictor arrays consisting of columns of word presentation trials, and rows corresponding to different neuroanatomical locations coded the occurrence of ripple events. The training arrays were compared with the outcome arrays, containing the behavioral recall results (no recall: 0, yes recall: 1), from all the subjects using a naïve Bayesian model (fitcnb.m). The two dimensional predictor arrays were initialized with empty cell values. The absence of a ripple was coded '0', true ripple on spike '1', spike '2', and ripple on oscillation '3'. In the case of multiple events occurring within a single region, codes of descending order (i.e. 1,2,3) took precedence. If a given subject did not have coverage of a neuroanatomical region that row contained all empty cells. The training arrays and outcome arrays, containing the behavioral recall results, from all the subjects were concatenated along with a subject code array reference. The model was subsequently probed to determine the change in the posterior probability of recall at individual neuroanatomical locations for each event type. B. The outcome arrays were then permuted but the total number of words recalled per session were preserved. Following each permutation, a Naïve Bayesian probabilistic model was constructed and the change in the posterior probability of recall at individual neuroanatomical locations was assessed. The results from the probabilistic models derived from the permuted data were used to derive a distribution of values for change in posterior probability for each neuroanatomic location and each event type. The significance of ripple occurrence during encoding was then be derived on the basis of the change in posterior probability value calculated for the actual outcome array, relative to this distribution, while the effect size or change probability was derived from the original model.

Power Analysis

Preprocessing: Visual inspection of beta and high gamma oscillations was conducted first to check for the presence of oscillations, using Brain Quick (Micromed S.p.A., Treviso, IT). Data from the distractor period was first restructured into contiguous 2-second "trials" to mirror the structure of the data from the encoding epoch. Fieldtrip (Oostenvald et al, 2011) was used to then perform initial processing steps on the iEEG data, in this case consisting of de-meaning.

Time-Frequency Analysis

Fieldtrip was used to compute time-frequency (TF) spectrograms for each individual trial, from either 12 to 40 Hz for the beta band analysis, or 65 to 250 Hz for the high gamma band analysis. Spectrograms were calculated using Morlet wavelets method with a wavelet width of 20 for high gamma, and 10 for beta band. This translates into a spectral bandwidth of approximately 5 Hz for beta band and 15 Hz for high gamma, and a wavelet duration of 120 ms for beta band and 50 ms for high gamma band. Spectral power was normalized by subtracting and then dividing by the mean over the whole 2-second period, resulting in a measure of "relative change".

Detection of Stimulus-Induced Responses

Following the computation of TF spectrograms for each trial, the mean TF was generated for a given subject-task-electrode combination. In order to identify potentially significant stimulus-induced responses in the TF plot, time series were generated by averaging the TF plot over 20 Hz intervals, overlapping by 10 Hz (for high gamma; for beta: 4 Hz intervals, overlapping by 2 Hz). The resulting time series were then z-scored by subtracting the pre-stimulus mean power and dividing by the standard deviation. Any period of the time series exceeding an absolute value z-score of 2 for greater than 50 ms was marked. After performing this procedure over the whole TF plot, a region of potentially significant stimulus-induced response was identified.

This potentially significant region was then used as the input region to a non-parametric statistical test with cluster-based multiple comparisons correction, of the encoding epochs compared to the distractor epochs. This statistical test was performed using Fieldtrip, following the procedure outlined in Maris & Oostenvald, 2007. In brief, a large number of random reshufflings are performed (here, number of randomizations=500), randomly re-assigning trials as either encoding or distractor. For each reshuffling, difference maps are then computed, generating a t-score difference map. This is thresholded at a given alpha level (here alpha=0.1) after which clusters are identified. The t-scores of the difference map are summed over each cluster, and the largest such sum is recorded. These cluster sums are used as the null distribution against which the cluster sums of the true difference map are compared. Monte Carlo estimates of the p-values are calculated for each cluster of the true difference by counting the percentage of randomly-generated cluster sums that is larger. If there were any significant (p<0.05) clusters resulting from this test, then further statistical testing was performed to compare the encoding epochs of subsequently recalled words ("recalled trials") to those of subsequently unrecalled words ("unrecalled trials").

Comparison of Recalled and Unrecalled Trials

Spectrograms of recalled and unrecalled trials for a given subject-task-electrode combination were compared in an identical fashion as described above: first, a region in time-frequency space of potentially significant induced response was identified in the overall mean TF plot; second: within this region, recalled trials were compared to unrecalled trials using the same non-parametric testing described above, resulting in Monte Carlo estimates of p values for clusters in the TF plot.

Classification by Logistic Regression

To test the predictive value of the significantly different clusters (recalled vs. unrecalled trials) in predicting recall success, we used the Matlab (Natick, MA) 'fitglm' function to implement a logistic regression model. This model was also applied to examine the effect of brain stimulation on memory performance on the basis of splitting the stimulated word encoding trials in to two groups: 1) stimulation applied following a word encoding trial with predicted recall failure, and 2) stimulation applied following a word encoding trial with predicted failure.

First, for each subject-task-electrode combination, it was determined if there were any significantly different clusters between recalled and unrecalled trials. If there were, any additional electrodes from the same task that showed a significant stimulus-induced response were included in the model. For each of these electrodes, high gamma and beta band power was calculated separately for each trial according to the following procedure: if there was a significant difference ($p<0.05$) between recalled and unrecalled trials, then for each trial spectral power was averaged over the region in time-frequency space containing this significant difference, resulting in a power vector of length(# of trials). If there was no significant difference, then spectral power was averaged over the region of most significant induced response. Since this was performed for high gamma and beta band separately, the number of resulting feature vectors was 2×(# of electrodes).

Next, we implemented the logistic regression model to estimate the probability of recall success on a distinct test set of encoding trials. We used the high gamma band and beta band vectors of power as predictors. In order to evaluate the performance of the classifier, we plotted the ROC using the estimated probabilities as scores. The area under the ROC (AUROC) was used as an evaluation metric.

Interaction of Effect of Stimulation and Encoding Classification

We next sought to determine whether the classification algorithm could help predict whether subsequent stimulation would be more or less successful. In an example subject (R1069M) who had completed the categorized free recall task both on and off stimulation, we first trained a logistic regression classifier on the unstimulated task, as described above, with the only difference being that the classifier was trained on all trials of the unstimulated task. We next tested this classifier on the stimulated task, using the same regions of interest in time-frequency space generated from the unstimulated task, and the associated classifier, to predict whether each trial was either recalled or unrecalled.

Correlation Between Recall Number and Recall-Epoch High Gamma (65-250 Hz) and Beta Power (14-30 Hz)

We tested for a correlation between high gamma and beta power during the recall epoch, and the number of words recalled during that period. Specifically, for each complete session there were 25 data points corresponding to the 25 blocks, and the 25 recall periods that occur at the end of each block. Since there were 12 words per block, recall number ranged from 0 to 12. High gamma band power was calculated across the entire 30 second recall period, which was input into a linear regression model, along with recall number, to calculate the relationship between high gamma power and recall number. Multiple comparisons correction was performed using a false discovery rate algorithm (Benjamini & Hochberg, 1995) on the resulting p values from all 281 subject-task-electrode combinations.

Identification of High-Gamma in Left BA40 as a Candidate Biomarker of Memory Performance In this portion of the study we asked if spikes and high-frequency oscillations (HFO) that spontaneously occur during word presentation in a free recall list learning task decrease the probability of recalling that word correctly. The patient cohort included 181 subjects who consented to undergo intracranial monitoring and participate in the task. Intracranial EEG was recorded at 500-1600 Hz and analyzed using a spike and HFO detector utilizing a topographical analysis of the depth iEEG wavelet convolution. We quantified spike and HFO events during 118,892 word encoding trials, and confirmed spike and HFO detections using visual validation and annotation editing. The electrode sites were classified using co-registered pre-implant MRI and post-implantation CT images that were segmented on the basis of several published brain atlases. A naive Bayesian machine learning model was used to calculate the posterior probabilities of word recall given a spike or HFO, and the significance of this prediction was determined using bootstrapping. In the left hemisphere, but not the right, ripples ($p<0.01$), and spikes ($p<0.01$) disrupted word encoding. In the left temporal neocortex, spikes in the middle temporal gyms decreased the probability of correct word recall by 11.9% (FIG. 1-3, $p<0.001$, $n=1,379$). In the left mesial temporal lobe, spikes did not disrupt verbal memory encoding in area CA1 (FIG. 1-3, $p>0.05$, $n=364$) nor in the dentate gyrus ($p>0.05$, $n=417$). However, spikes in the left entorhinal cortex (FIG. 1-3, prob=−54.2%, $p<0.001$, $n=81$) and perirhinal cortex (FIG. 1-2, prob=−15.6%, $p<0.01$, $n=167$) did strongly disrupt memory encoding. Encoding was not disrupted by spikes in right mesial temporal lobe structures. These results suggest that normal physiological function in the left entorhinal and perirhinal cortices are required for verbal memory encoding. Also, verbal memory impairment in patients with mesial temporal lobe epilepsy may be attributed, in part, to inter-ictal epileptiform activity in the left entorhinal and perirhinal cortices. Using the naïve Bayesian machine learning model we also observed that only in left BA40 did ripple oscillations result in an increase in the probability of recall (FIG. 1-2, prob=+65.7%, $p<0.05$, $n=53$, FIG. 1-3).

Human Visual Inspection of the Left BA40 Intracranial EEG

We further investigated whether the ripple oscillations in left BA40 which occurred during encoding and correlated with an increase in the probability of recall represented physiological and not pathological high-gamma oscillations that are involved with encoding new memories and may serve as a biomarker of human memory performance by visually inspecting the intracranial EEG from 281 subject-task-electrode combinations from 35 subjects in BA40 (FIG. 4). Of these, 99 were depth electrode contacts and 182 were subdural electrodes (153 grid and 29 strip). The number of task-electrode pairs analyzed per subject ranged from 1 to 30. This dataset was then analyzed for the presence of stimulus-induced high gamma and beta band activity during the word encoding period, as well as significant differences between the induced response for words subsequently recalled versus words subsequently not recalled (a.k.a. subsequent memory effect). Visual inspection of the iEEG demonstrated oscillations (65-250 Hz) that were longer in duration, as compared to ripple events, during word presentation, and were classified as high-gamma activity (Canolty et al., 2006). This type of high-gamma does not have pathological significance, but rather, in this case, was associated with memory encoding in left BA40. Qualitatively, we observed a subsequent memory effect for the properties of the high-gamma activity in left BA40 (FIG. 5) suggesting that high-gamma in left BA40 is a biomarker of memory performance. We also qualitatively observed the beta activity in left BA40 exhibited a subsequent memory effect indicating that it was also a biomarker of memory performance.

Power Analysis: High Gamma

To quantify our observation that the properties of high-gamma (65-250 Hz) oscillations in left BA40 are biomarkers of human memory performance and determine the statistical significance of this finding we utilized a time-frequency analysis of the iEEG associated with each word encoding trial. We first asked whether word presentation was associated with an induced positive or negative modulation of activity in the high-gamma (80-250 Hz) band. We then asked if this induced response exhibited a subsequent memory effect.

Figure 6:
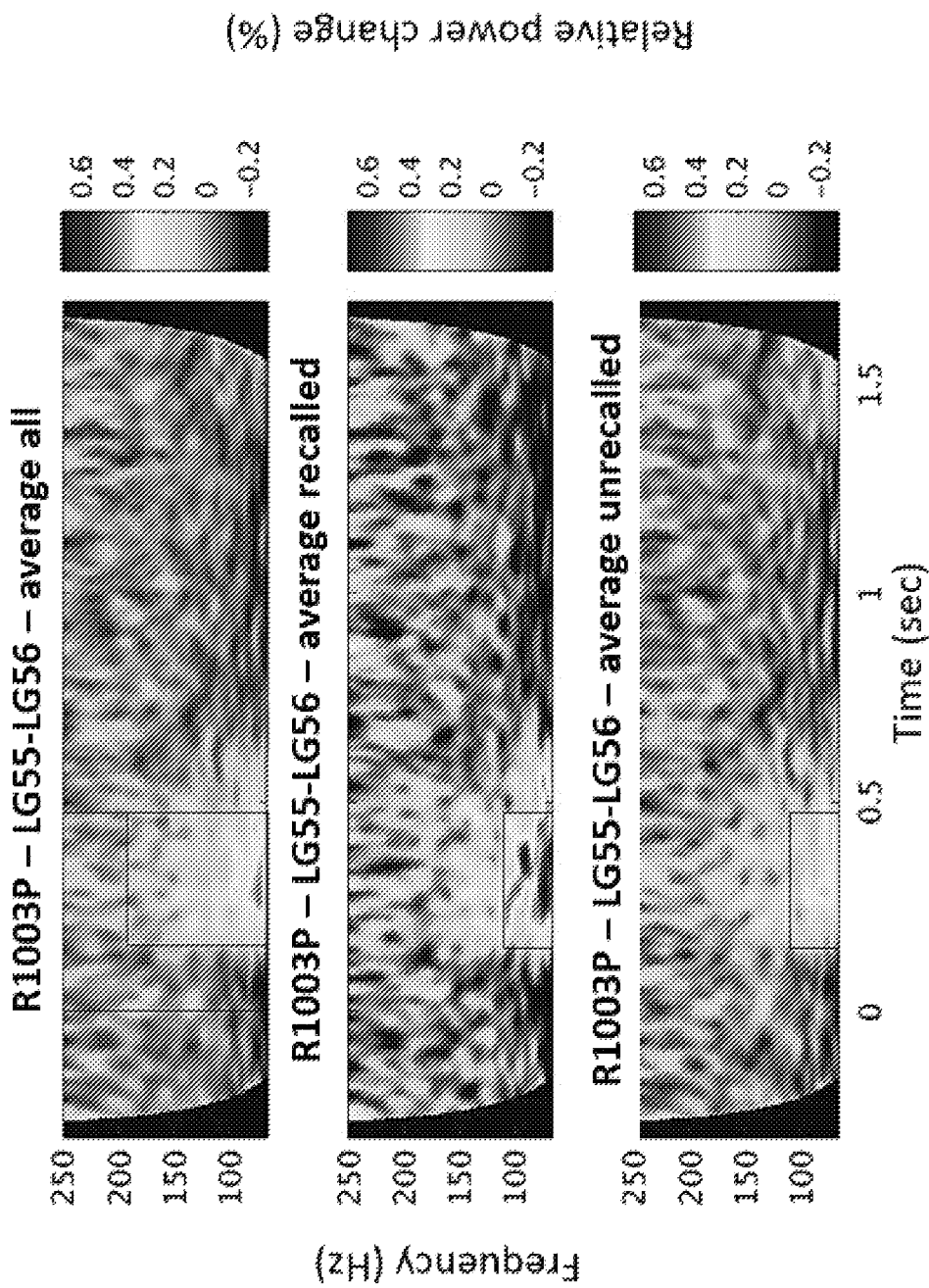
FIG. 6 depicts an example average time-frequency plot of encoding epochs during which a positive stimulus-induced high gamma band response with a subsequent memory effect is observed.

Most subjects had at least one electrode from one task that showed a significant stimulus-induced response (FIGS. 6 and 7 top): out of the 281 electrode contacts from 35 subjects, 124 electrode contacts from 32 subjects showed a statistically significant response when compared with the distractor period (Monte Carlo estimate with cluster-based multiple comparisons correction, $p<0.05$). Of these 124 contacts, 69 showed a positive, and 66 showed a negative induced response. Eleven showed both positive and negative responses. The stimulus induced response serves as a way of identifying encoding state, and differentiating them from recall state. Accordingly, we can evaluate and identify the difference between encoding (thus predictive of improved memory) versus recall (predictive of providing output of the encoded memory).

Figure 7:
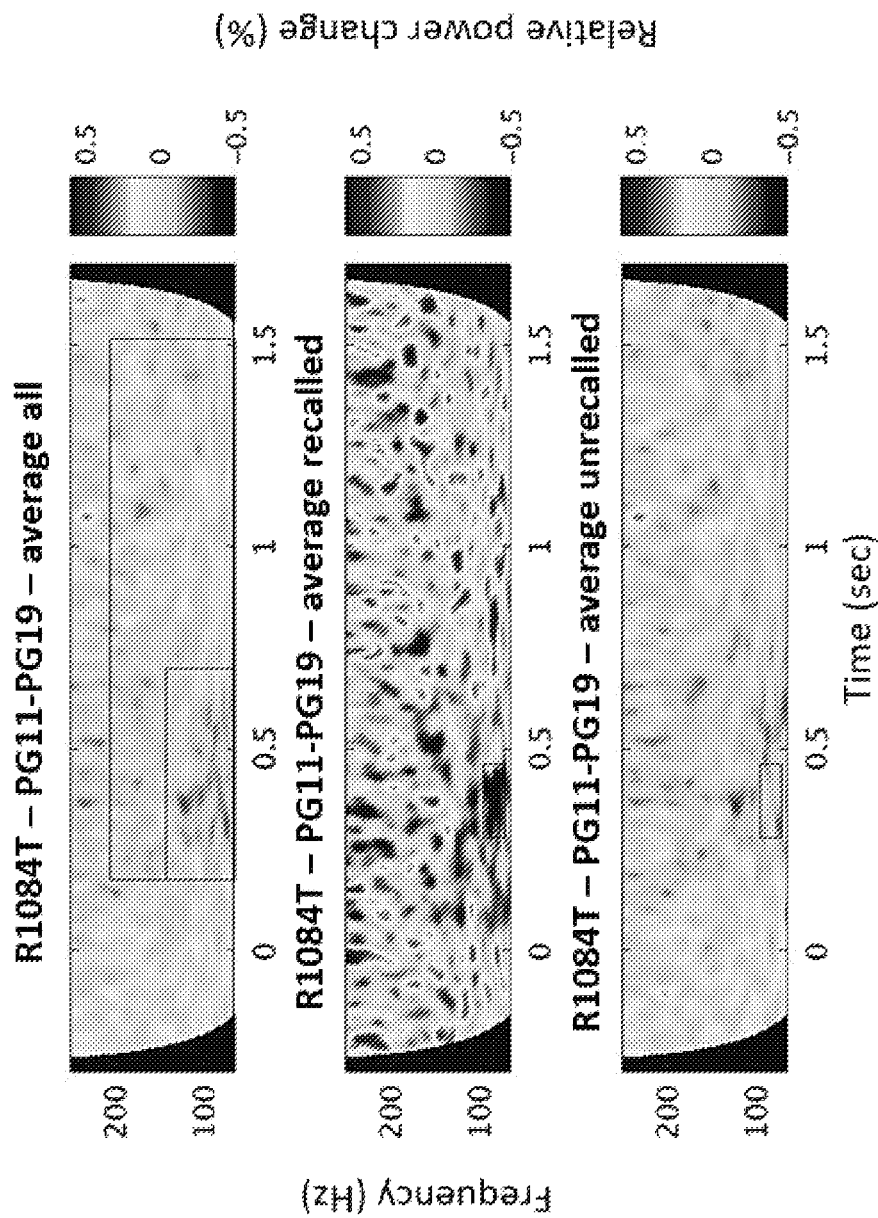
FIG. 7 depicts an example average time-frequency plot of encoding epochs during which a negative stimulus-induced high gamma band response with a subsequent memory effect is observed.

Among this subset of 124 electrodes showing significant stimulus-induced responses, 18 electrodes from 13 subjects showed a significant difference between responses of subsequently recalled and unrecalled words (Monte Carlo estimate with cluster-based multiple comparisons correction, $p<0.05$). Twelve of the 18 electrodes showed positive induced responses (FIG. 6 middle, bottom), and eight showed negative responses (FIG. 7 middle, bottom).

Most electrodes showed congruent effects (i.e. the sign of the induced response was in the same direction as the recalled minus unrecalled effects (FIG. 6,7)), but some also showed incongruent effects. Ten of the 18 electrodes showed congruent effects, 5 showed incongruent effects, and 3 showed both. Among the 10 electrodes showing congruent effects, 8 were positive, with greater responses for recalled compared with unrecalled, and 2 were negative. Among the 5 showing incongruent effects, 4 showed negative induced responses.

In terms of positive and negative subsequent memory effects (SME), of the 18 electrodes showing significant differences between recalled and unrecalled trials (Monte Carlo estimate with cluster-based multiple comparisons correction, $p<0.05$), 15 showed positive SMEs and 4 showed negative SMEs (1 showed both).

Power Analysis: Beta

Figure 8:
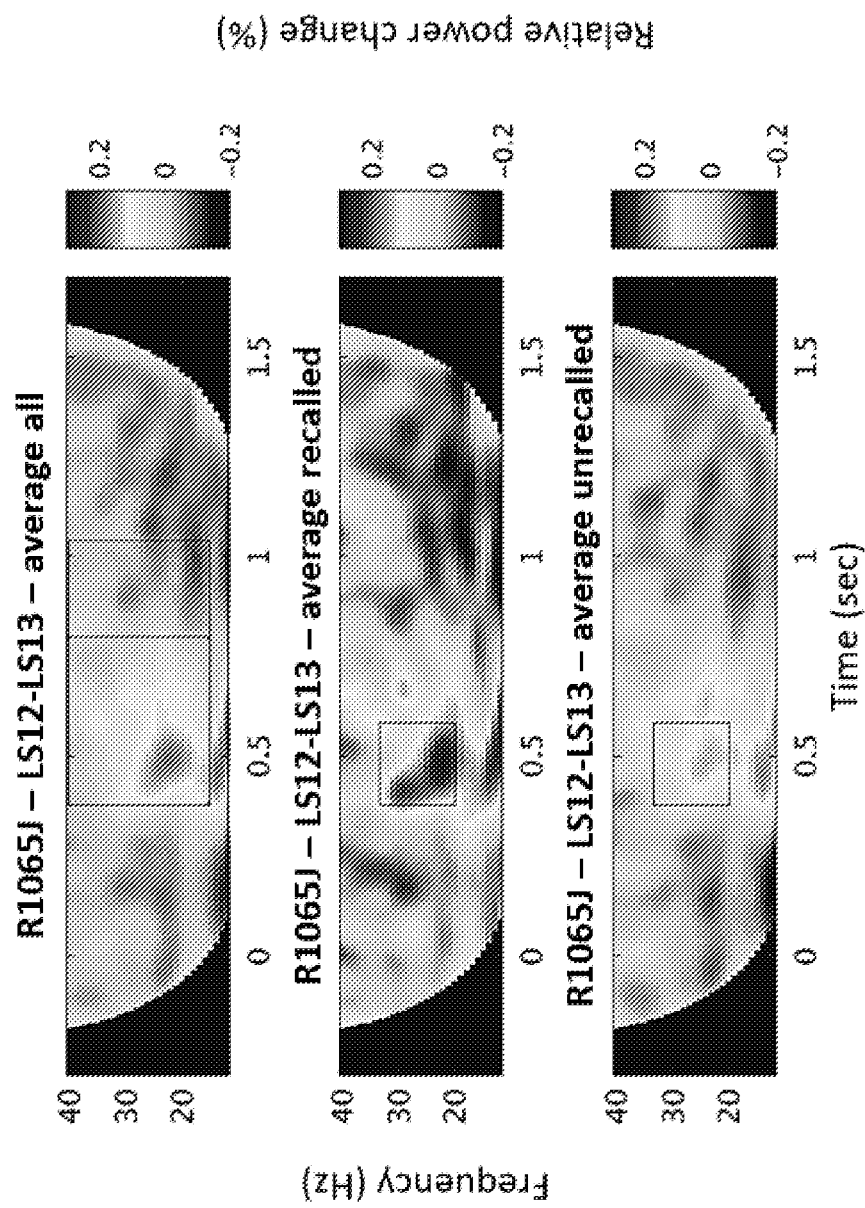
FIG. 8 depicts an example average time-frequency plot of encoding epochs during which a positive stimulus-induced beta band response with subsequent memory effect is observed.
Figure 9:
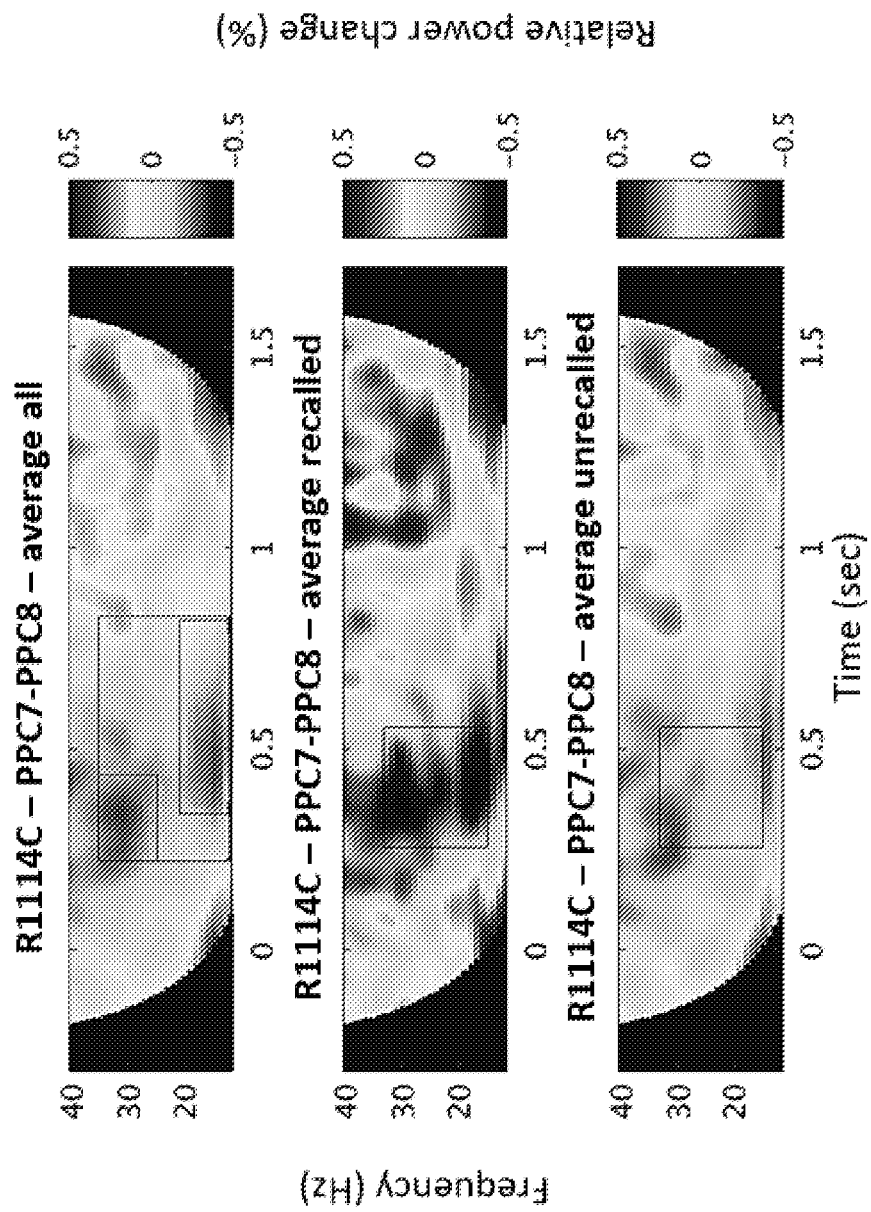
FIG. 9 depicts an example average time-frequency plot of encoding epochs during which a negative stimulus-induced beta band response with subsequent memory effect is observed.

Similar numbers of electrodes showed stimulus-induced beta band (14-30 Hz) responses. Of the 281 electrodes, 125 from 28 subjects showed significant responses (FIG. 8, 9 top). In comparison to the high gamma band, a greater percentage of electrodes showed negative induced responses in the beta band (FIG. 9 top). Of the 125 showing significant (Monte Carlo estimate with cluster-based multiple comparisons correction; $p<0.05$) responses, 72 showed significant positive responses, 89 showed significant negative responses, and 36 showed both.

Among the subset of electrodes showing significant responses, 10 electrodes from 7 subjects showed a significant difference between recalled and unrecalled trials (Monte Carlo estimate with cluster-based multiple comparisons correction, $p<0.05$). Six of those 10 showed positive induced responses (FIG. 8 middle, bottom), and 5 showed negative (FIG. 8 middle, bottom) and 2 showed both. In terms of the congruency between the sign of the induced response and the recalled minus unrecalled direction, 5 showed congruent, 2 showed incongruent, and 3 showed both incongruent and congruent effects.

Temporal Analysis of Stimulus-Induced Responses:

We compared the positive and negative induced responses also by the times of their maxima; there were no differences, as illustrated by the almost identical histograms of times of maxima, which were at ~500 ms post-stimulus. This was the case in both high gamma and beta bands.

Spatial Analysis of Stimulus-Induced Responses

Figure 10:
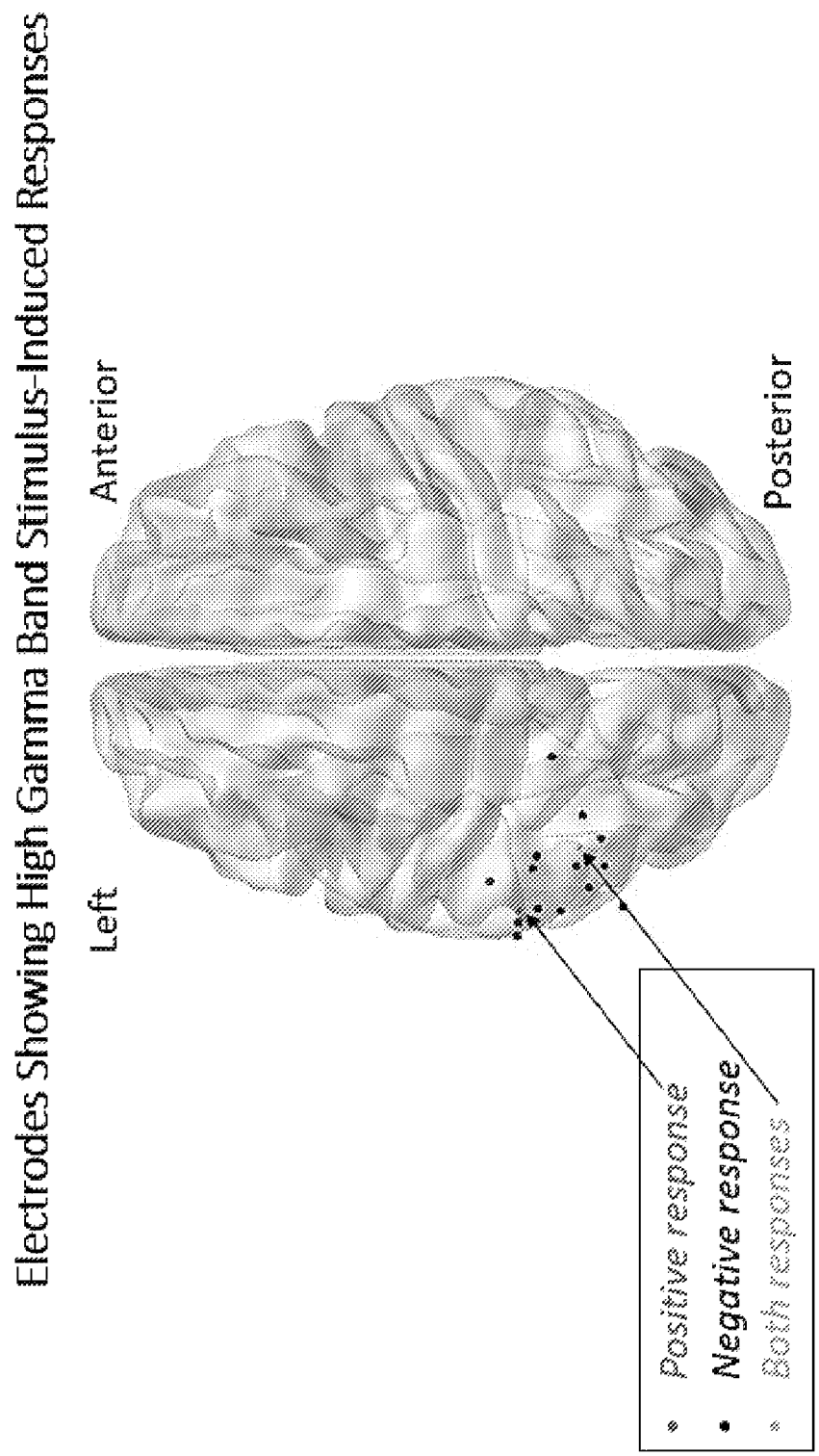
FIG. 10 depicts axial illustration of locations of electrodes that showed significant high gamma subsequent memory effects, colored by the direction of the stimulus-induced high gamma band responses of that electrode.
Figure 12:
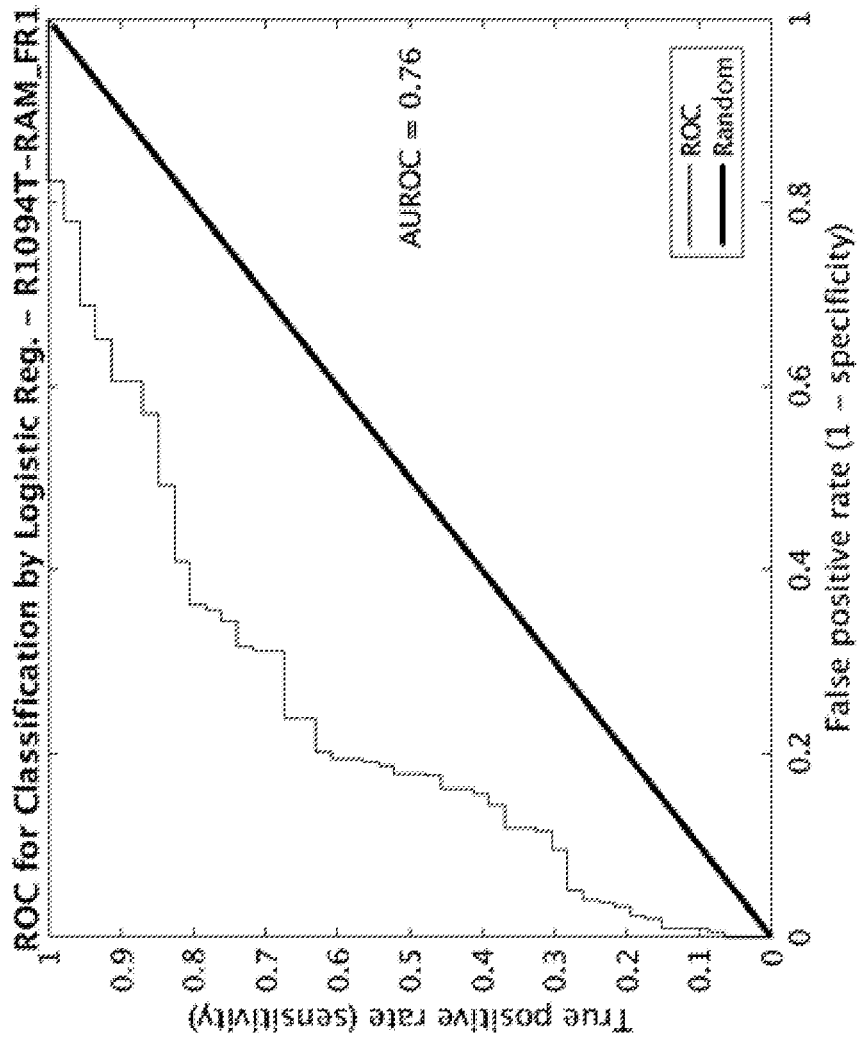
FIG. 12 depicts a plot of the receiver operating curve from the logistic regression classifier of recall success using left BA40 high-gamma and beta oscillation biomarkers for patient R1094T.

We compared the Talairach coordinates of electrodes exhibiting positive responses to those exhibiting negative responses. When examining high gamma band responses, electrodes showing positive responses were significantly more anterior (2-sample t-test; $t(133)=4.57$; $p<0.001$, FIG. 10). This remained true when restricting to electrodes that showed a significant difference between recalled and unrecalled trials. For beta band responses there was no such effect.

Classification of Encoding Activity

We tested the performance of a logistic regression model for classifying encoding-related activity in left BA40 as belonging to either subsequently recalled or unrecalled words. For each subject-task pair that showed significant high gamma or beta band differences between recalled and unrecalled words in any electrode, all electrodes for that task that showed a significant stimulus-induced response were used in the classification. High gamma and beta power over the regions of significantly different high gamma and beta band activity between recalled and unrecalled trials were used as features. Classifiers for 16 unique subject-task pairs were computed on a training set of word encoding trials and then evaluated on a distinct test set of word encoding trial. The Area under the ROC (AUROC) for predicting recall success on the basis of the high-gamma and beta properties during the encoding trial was computed as an evaluation metric. AUROC values ranged from 0.57 to 0.76 (mean=0.65) and were greater for subjects who showed significant high gamma differences between recalled and unrecalled trials (FIG. 11,12), compared to those who only showed significant beta band differences (0.69 vs. 0.60).

Enhancing Memory by Brain Stimulation During Human Memory Performance States Defined by Left BA40 High-Gamma (65-240 Hz) and Beta (14-30 Hz) Biomarkers.

Example subject 1069M completed two sessions of the same task (CatFR), one in which there were no stimulation trials (CatFR1), and one in which stimulation was applied to 120 out of 300 trials (CatFR2). All following results are from the stimulated task, CatFR2. Of the 300 trials in this task, 180 did not have stimulation applied. Of these 180, 66 were classified as recalled and 114 were classified as unrecalled. Among the 66 classified as recalled, 25 were actually recalled (38%). Among the 114 classified as unrecalled, 38 were actually recalled (33%).

Figure 13:
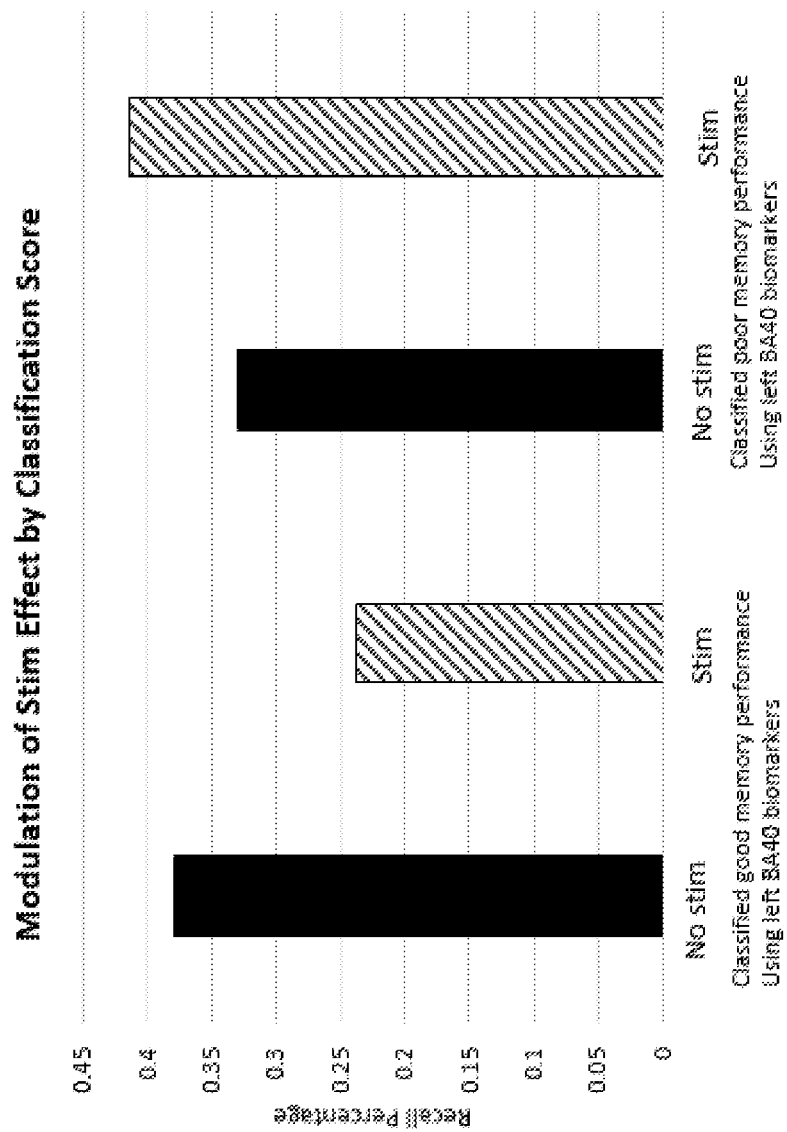
FIG. 13 depicts the effects of brain stimulation during memory encoding on recall performance depending on the memory performance measure defined by high-gamma and beta band oscillation properties in left BA40 during encoding.
Figure 15:
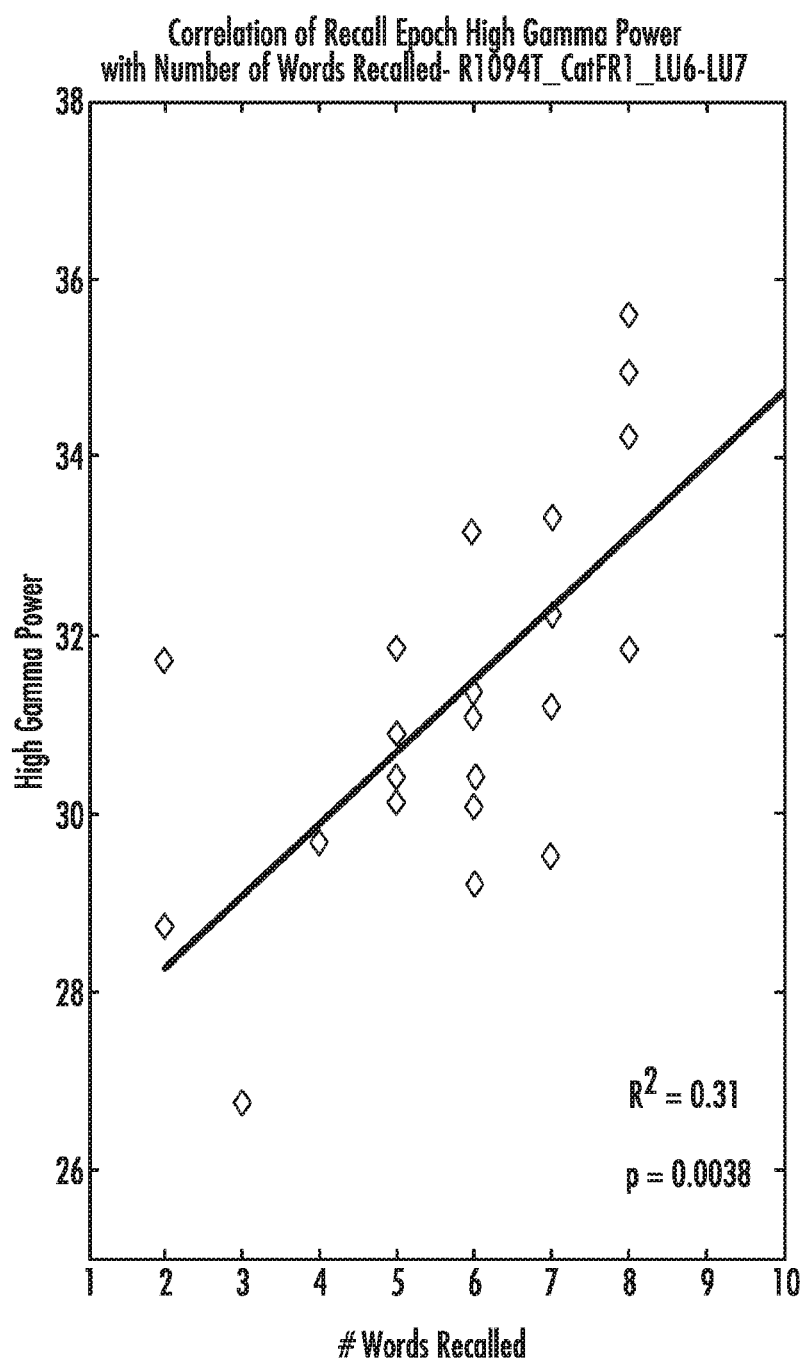
FIG. 15 depicts an example of the statistically significant linear correlation between high-gamma (65-250 Hz) power measured from left BA40 during the recall epoch and the number of words recalled.
Figure 17:
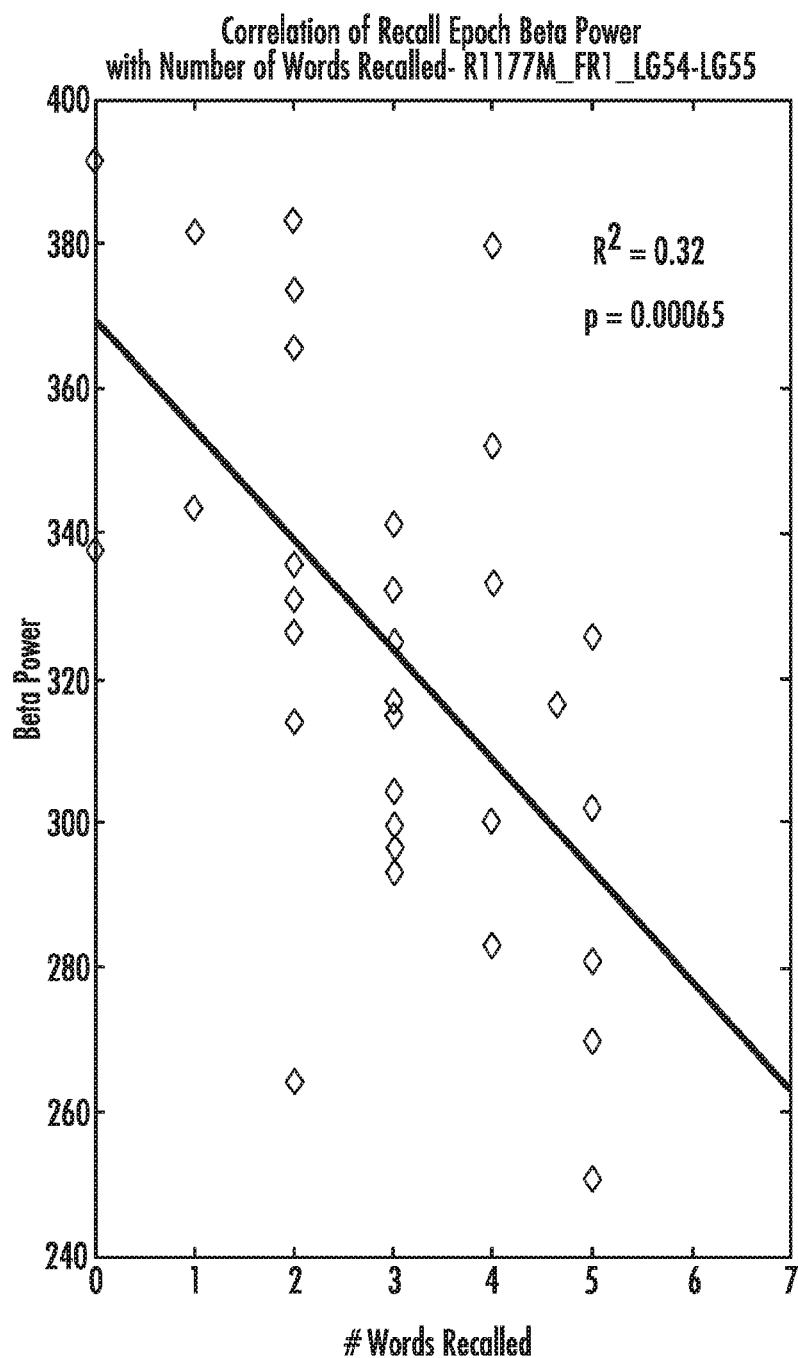
FIG. 17 depicts an example of the statistically significant linear correlation between beta (14-30 Hz) power measured from left BA40 during the recall epoch and the number of words recalled.

We then examined unstimulated trials that immediately preceded stimulation, and noted whether the unstimulated trial was described as reflecting strong or weak memory performance by the classifier that utilized the high-gamma and beta-band biomarker oscillation properties in left BA40. There were 50 unstimulated trials that immediately preceded a stimulated trial. Of the 50 associated stimulation trials, 17 were classified as good memory performance. We hypothesized that stimulation following a trial that was classified as poor memory performance would have more of an effect than stimulation following a trial that was classified as good memory performance. We found that among stimulated trials that immediately followed an unstimulated trial, the recall percentage was greater when the preceding unstimulated trial was classified as poor memory performance (i.e. unrecalled), compared to when the unstimulated trial was classified as good memory performance (i.e. recalled (41% vs. 24%, FIG. 13)).

Correlation of Recall Percentage with Recall-Epoch High Gamma Power

We examined the relationship between high gamma band power during the entire 30 second recall period, and the number of words recalled. Twenty-four task-electrode pairs from 8 different subjects showed significant correlations after multiple comparisons correction (16 depth, 8 subdural), 22 of which were positive correlations (FIG. 14,15). Of these 24 task-electrode pairs, 13 showed significant stimulus-induced high gamma responses, and 2 additionally showed significant differences between recalled and unrecalled encoding trials.

Correlation of Recall Percentage with Recall-Epoch Beta Power

We also examined the relationship between beta band power during the entire 30 second recall period, and the number of words recalled. Eight task-electrode pairs from 4 different subjects showed significant correlations after multiple comparisons correction, 5 of which were positive correlations (FIG. 16,17).

Preferred Embodiments

The report generated by the method includes the electrode locations, or identifiers, and the beta (14-30 Hz) and high-gamma (65-240 Hz) oscillations detected within a predefined temporal interval using the topographical analysis of the wavelet convolution at each of these locations in left BA40. Specifically, the report includes the onset and offset times of the beta and high-gamma oscillations, the beta and high-gamma oscillation power, spectral content, and duration. The report can be used to generate annotations of the EEG record. The annotated EEG can be visually interpreted by a clinician to guide clinical decision making, and a therapeutic procedure such as [1. Respective or thermally ablative epilepsy surgery, 2. gene therapy, 3. cell therapy, 4. Or placement of a device that records or stimulates the brain with electricity, magnetic fields, or optogenetic stimulation] can be selected and targeted on the basis of the human visual inspection of the computer annotated EEG record. The report generated by the method can also include, a measurement of human memory performance that is derived by classifying the subject's memory performance on the basis of a comparison of the biomarkers that include left BA40 beta (14-30 Hz) and high-gamma (65-250 Hz) oscillations' properties with the subject's prior human memory performance and the properties of the biomarkers (i.e. left BA40 beta (14-30 Hz) and high-gamma (65-250 Hz) oscillations) corresponding to the past memory performance; this report can be presented to the clinician or another software process, in the absence of the original EEG record, to target a therapeutic procedure such as the placement of a device that records or stimulates the brain with electricity, magnetism, or optogenetic stimulation.

Figure 18:
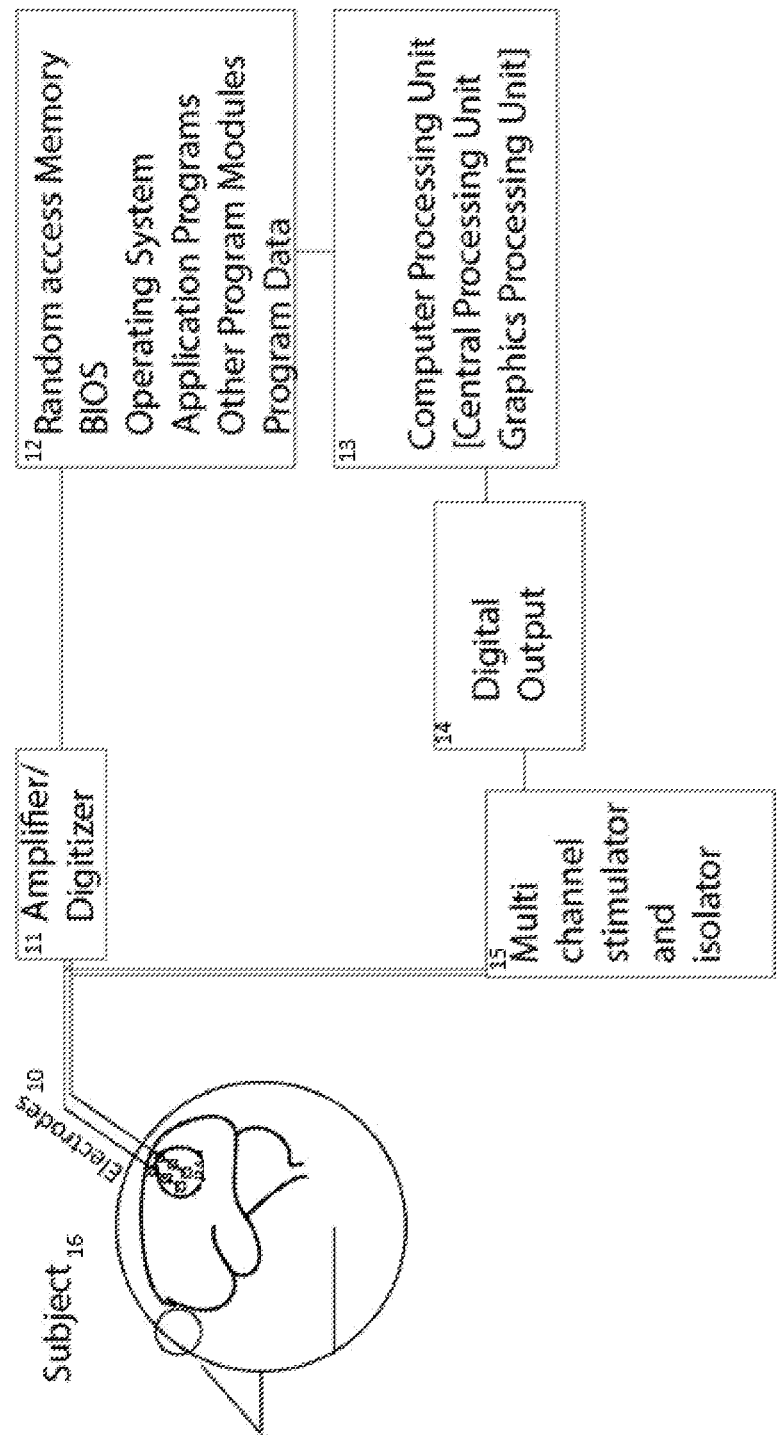
FIG. 18 depicts a diagram of the device for capturing electrical signals from left BA40 for performing an embodiment of the method described herein.

A preferred embodiment is depicted in FIG. 18, comprising a device composed of a) a subject with a plurality of electrodes 10; b) a brain signal acquisition device (Amplifier/digitizer) 11 to record electrical signals from multiple locations of a subject; c) a non-transitory computer-readable memory storing instructions executable 12 by the computer processor 13; d) a computer processor 13; e) digital outputs 14; f) a multichannel stimulator 15; and g) a subject 16 with a plurality of brain stimulating electrode(s). The computer processor; and a non-transitory computer-readable memory storing instructions executable by the computer processor; are configured to execute the method applied to the brain signals recorded by the plurality of the electrodes, for example include the RAM, BIOS, an operating system, application programs, program data, and other program modules as necessary to implement and run the system. The report generated by the method is translated by the computer processor and computer-readable memory in to a train of TTL pulses transmitted by the digital output. A multichannel stimulator connected to the digital output reads the TTL pulses and electrically stimulates the brain by generating current that is transmitted via the brain stimulating electrode.

The required features of the preferred embodiment are that the device can detect and stimulate left BA40, or other brain regions, with therapeutic regimens to enhance human memory performance, which can be confirmed by modification of the beta (14-30 Hz) and high-gamma (65-250 Hz) oscillations in left BA40. The report generated by the method identifies, and characterizes each high-gamma (65-240 Hz) and beta (14-30 Hz) oscillation biomarker in a predefined temporal interval and determines the associated human memory performance measurement. Thus, the report generated by the method can be utilized by the preferred embodiment to determine when and where left BA40 engaged in memory related activity, and the relative performance of this activity. On the basis of this report a certain regimen of stimulation can be delivered to a certain site within left BA40 or other brain region. The preferred embodiment can comprise a device that is worn or implanted in the patient. In another embodiment, the digital output from the system can trigger an environmental stimulus such as an audio or visual information that provides biofeedback. In another embodiment, the digital output from the system is used for a cognitive brain computer interface.

In certain studies, a patient population was tasked with certain memory tasks during a standardized neurophysiological assessment. As used herein, this term means a pre-determined neurophysiological assessment that is replicable among a patient population. Individual protocols may be different from one to another, so long as the same assessment is utilized consistently when comparing data. For example a set of images may be displayed to an individual comprising pictures, words, or other features. The image remains displayed for a short amount of time—1-10 seconds, typically, and then a distractor is provided. After the distractor, a patient is asked to recall the images. A numerical score can be generated based on the percentage of images that are correctly recalled. The individual may have to state the images, or provided with examples to determine if they were shown or not shown the image, or a multiple choice option.

Accordingly, in one example, a patient population was assessed and data from the high gamma and beta oscillations from the left BA40 collected. To evaluate the modification of memory, we applied an electronic pulse to the brain, wherein said electronic pulse modified the left BA 40. By application of the appropriate electronic pulse during encoding or recall status of a memory, we can alter and improve the memory encoding and alter and improve the memory recall.

Therefore, the biomarkers generated herein allow quantification of qualitative performance of memory. Accordingly, we can test memory function over time, or as a comparison between an individual and a group of patients. Thus, we pooled data for patients of the same gender, and within an age bracket of 1, 2, 3, 5, 7, 10, 15, or 20 years, and generated a baseline model of the biomarkers during encoding and during recall. By modifying the size of the data pool, you can create smaller error bars. Similarly, reducing the age variation, you can create smaller error bars. Accordingly, we can generate an appropriate baseline data regarding the performance on memory tasks. Once the baseline model is created, we can utilize it to compare and quantify the level of memory function, either on a 0-100 scale, above or below the mean, on a bell-curve, or the like. For example, in 0-100 refers to a scale of memory formation or recall as compared to a patient population. Thus, 0 refers to a near absence of memory recall or formation. A 50 would refer to median memory and 100 would be perfect memory. In practice these ranges fall within a bell curve. This allows us to differentiate from a binary point (good or poor memory) to a scale that allows relative performance as compared to a known pool of data.

This comparison is important as we can then give a quantitative measure as to the performance of an individual. For example, a person aged 65 is in a profession that requires retirement at age 65. A person could prove that their memory performance is equivalent to someone of age 55, as a measure of their relative cognitive performance and bolster an argument that no retirement is mandated.

However, the devices and methods used herein have substantial additional far reaching applications. For example, a device of the present embodiments may be attached to an individual. The device measures the biomarkers in the left BA 40, specifically the high gamma and the beta oscillations. The device and signal processing can be utilized to measure memory performance over time. For example, the person has better memory in the morning than in the evening, as so electrical stimulus can be applied only during the morning, when certain signals are activated to increase performance.

Similarly, a device can be used to detect and measure modifications over time for the individual. For example, certain patients in our data pool were taking therapeutics that altered memory function. By using a device attached to the patient and recording data for these biomarkers, we can evaluate the efficacy and effects of the therapeutic over time. Thus, as a drug discovery tool, the device can be worn by an individual, a baseline performance is generated and calculated. The person is provided with a therapeutic for a predetermined amount of time. During this predetermined amount of time, the device continues to measure the biomarkers. We can then generate a plot of the biomarkers, over time, during the predetermined amount of time while taking the therapeutic. A comparison between the baseline or control (placebo) subjects could quantitatively describe the memory improvements, which heretofore were not possible. Accordingly, we envision methods of drug discovery and methods of quantification of improvements in memory performance through application of the device and methods described herein.

What is claimed is:

1. An automated method for monitoring human memory performance in a subject by recording electroencephalographic activity from the left Brodmann Area 40 (BA40) of the subject using an electrical sensing device comprising a plurality of electrodes, and performing operations, by one or more processors, including:
   detecting and capturing electrical signals from the left BA40 using the electrical sensing device;
   applying wavelet convolutions to the captured electrical signals to generate a time-frequency representation using Morlet wavelets method with a wavelet width of 20 for high gamma (65-250 Hz), and 10 for beta band (14-30 Hz);
   determining a region or regions of the time-frequency representation that corresponds with high-gamma band oscillations on the basis of a predetermined threshold of $1*10^7$ arbitrary units or equivalent;
   characterizing properties of the high-gamma band oscillations including onset, offset, power, duration, and spectral content using a topographical analysis of the wavelet convolution;
   determining a region or regions of the time-frequency representation that corresponds with beta band oscillations on the basis of a predetermined threshold;
   characterizing properties of beta band oscillations including, onset, offset, power, duration, and spectral content using a topographical analysis of the wavelet convolution;
   determining properties including onset, offset, power, duration, and spectral content of all high-gamma and beta band oscillations during a predetermined epoch of electrical signals recorded from the plurality of electrodes;
   classifying the subject's memory performance on the basis of a comparison of the oscillations' properties with a prior human memory performance from the subject and properties of oscillations corresponding to the prior human memory performance;
   generating a report of the subject's current and past memory performance and the properties of the corresponding oscillations; and
   executing instructions to cause a therapeutic device to administer, without user intervention, a therapy at a predetermined location, the therapy being based on the report.

2. The method of claim 1, wherein using the electrical sensing device comprises using anon-invasive or minimally invasive electroencephalogram system.

3. The method of claim 1, wherein using the electrical sensing device includes using an intracranial electroencephalogram system.

4. A system for monitoring human memory performance based on recording electroencephalographic activity from the left Brodmann Area 40, said system comprising:
   a data acquisition device operative to receive an electrical signal from a sensing device operative to record electrical signals from multiple locations of a subject's left Brodmann Area 40;
   a storage system for storing instructions, the storage system comprising memory circuitry; and
   a microprocessor system communicatively coupled to the storage system, the microprocessor system being configured to execute instructions stored in the storage system to cause the system to:
record, using the data acquisition device, electrical signals from multiple locations in the left Brodmann Area 40 of the subject;
apply wavelet convolutions to the recorded electrical signals to generate a time-frequency representation;
determine a region or regions of the time-frequency representation that corresponds with high-gamma band oscillations on the basis of a predetermined threshold;
characterize the properties of high-gamma band oscillations including, onset, offset, power, duration, and spectral content based on a topographical analysis of the wavelet convolutions;
determine a region or regions of the time-frequency plot that correspond(s) with beta band oscillations on the basis of a predetermined threshold;
characterize properties of beta band oscillations including onset, offset, power, duration, and spectral content using a topographical analysis of the wavelet convolution;
determine properties including onset, offset, power, duration, and spectral content of all high-gamma and beta band oscillations during a predetermined epoch of electrical signals recorded from the multiple locations of the subject's left Brodmann Area 40;
classify the subject's memory performance on the basis of a comparison of properties of the oscillations with a prior human memory performance from the subject and properties of oscillations corresponding to the prior human memory performance; and
generate a report of the subject's current and past memory performance and the properties of the corresponding oscillations, wherein the report is informative for determination of para meters for a therapeutic procedure to improve human memory performance; and
wherein the microprocessor system is further configured to execute instructions stored in the storage system to cause the system to use a therapeutic device to administer, without user intervention, a therapy at a predetermined location, the therapy being based on the report.

5. The system of claim 4, wherein the data acquisition device comprises an implantable or wearable device.

6. The method of claim 1, further comprising:
implanting a therapeutic device in the subject, and using the therapeutic device to administer, without user intervention, therapy in response to the report, the report including of electrical signals at identified locations in the left Brodmann Area 40 displaying high-gamma and beta oscillations of a predefined onset, offset, power, duration, and spectral content.

7. The system of claim 4, wherein the therapy comprises electrical or electromagnetic stimulation.

8. The system of claim 4, wherein the therapy is optogenetic stimulation.

9. The system of claim 4, wherein the therapeutic device is operative to administer, without user intervention, environmental stimuli including an audio alert in response to the left Brodmann Area 40 displaying high-gamma and beta oscillations of a predefined onset, offset, power, duration, and spectral content.

10. The system of claim 4, wherein the prior human memory performance represents use of the system, under the same operational protocol, at a prior time.

11. At least one non-transitory computer-readable storage medium containing instructions that, when executed by a processor of a system for detecting and characterizing memory performance, cause the system to:
receive electrical signals recorded from multiple locations in the left Brodmann Area 40 of a subject using an electrical signal sensing device of the system;
record, using the electrical signal sensing device, electrical signals from multiple locations in the left Brodmann Area 40 of a subject;
apply wavelet convolutions to the recorded electrical signals to generate a time-frequency representation;
determine a region or regions of the time-frequency representation that correspond(s) with high-gamma band oscillations on the basis of a predetermined threshold;
characterize properties of high-gamma band oscillations including onset, offset, power, duration, and spectral content based on topographical analysis of the wavelet convolution;
determine a region or regions of the time-frequency plot that correspond(s) with beta band oscillations on the basis of a predetermined threshold;
characterize properties of beta band oscillations including onset, offset, power, duration, and spectral content using a topographical analysis of the wavelet convolution;
determine properties including onset, offset, power, duration, and spectral content of all high-gamma and beta band oscillations during a predetermined epoch of electrical signals recorded from the multiple locations of the subject's left Brodmann Area 40;
classify the subject's memory performance on the basis of a comparison of properties of the oscillations with a prior human memory performance from the subject and properties of oscillations corresponding to the prior human memory performance;
generate a report of the subject's current and past memory performance and the properties of the corresponding oscillations, wherein the report is informative for the determination of parameters for a therapeutic procedure to improve human memory performance; and
cause the system to use a therapeutic device to administer, without user intervention, a therapy at a predetermined location, the therapy being based on the report.

* * * * *